(12) United States Patent
Metz et al.

(10) Patent No.: US 10,772,948 B2
(45) Date of Patent: Sep. 15, 2020

(54) METHODS AND COMPOSITIONS FOR DENGUE VIRUS VACCINES AND DIAGNOSTICS

(71) Applicant: The University of North Carolina at Chapel Hill, Chapel Hill, NC (US)

(72) Inventors: Stefan Metz, Carrboro, NC (US); Aravinda Desilva, Chapel Hill, NC (US); Michael Miley, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 75 days.

(21) Appl. No.: 15/766,304

(22) PCT Filed: Sep. 20, 2016

(86) PCT No.: PCT/US2016/052706
§ 371 (c)(1),
(2) Date: Apr. 5, 2018

(87) PCT Pub. No.: WO2017/062174
PCT Pub. Date: Apr. 13, 2017

(65) Prior Publication Data
US 2018/0280494 A1    Oct. 4, 2018

Related U.S. Application Data

(60) Provisional application No. 62/238,496, filed on Oct. 7, 2015.

(51) Int. Cl.
| | | |
|---|---|---|
| *A61K 39/12* | (2006.01) | |
| *G01N 33/68* | (2006.01) | |
| *G01N 33/569* | (2006.01) | |
| *A61P 31/14* | (2006.01) | |
| *C07K 14/005* | (2006.01) | |
| *C12N 7/00* | (2006.01) | |

(52) U.S. Cl.
CPC ............ *A61K 39/12* (2013.01); *A61P 31/14* (2018.01); *C07K 14/005* (2013.01); *C12N 7/00* (2013.01); *G01N 33/56983* (2013.01); *G01N 33/6854* (2013.01); *C07K 2319/21* (2013.01); *C12N 2770/24122* (2013.01); *C12N 2770/24134* (2013.01); *C12N 2770/24151* (2013.01); *G01N 2333/185* (2013.01); *Y02A 50/386* (2018.01); *Y02A 50/388* (2018.01); *Y02A 50/39* (2018.01); *Y02A 50/394* (2018.01); *Y02A 50/396* (2018.01); *Y02A 50/53* (2018.01)

(58) Field of Classification Search
None
See application file for complete search history.

(56) References Cited

U.S. PATENT DOCUMENTS

| | | | |
|---|---|---|---|
| 2008/0268423 A1 | 10/2008 | Barrett et al. | |
| 2018/0280494 A1* | 10/2018 | Metz .................. | C12N 7/00 |

FOREIGN PATENT DOCUMENTS

| | | | |
|---|---|---|---|
| WO | WO 2014/074535 A2 | 5/2014 | |
| WO | WO 2016/012800 | * | 1/2016 |

OTHER PUBLICATIONS

Li et al. (Trends in Microbiology. Apr. 2014; 22 (4): 176-182).*
Bressanelli et al. "Structure of a flavivirus envelope glycoprotein in its low-pH-induced membrane fusion conformation" *The EMBO Journal* 23:728-738 (2004).
International Search Report and the Written Opinion of the International Searching Authority corresponding to International Patent Application No. PCT/US2016/052706 (8 pages) (dated Feb. 2, 2017).
Rey et al. "The envelope glycoprotein from tick-borne encephalitis virus at 2 Å resolution" *Nature* 375:291-298 (1995).
Zhang et al. "Structure of immature flavivirus particles" *The EMBO Journal* 22(11):2604-2613 (2003).
Dejnirattisai et al. "A new class of highly potent, broadly neutralizing antibodies isolated from viremic patients infected with dengue virus" Nature Immunology, 16(2):170-177 (2015).
Fibriansah et al. "A potent anti-dengue human antibody preferentially recognizes the conformation of E protein monomers assembled on the virus surface" EMBO Molecular Medicine, 6:358-371 (2014).
Fibriansah et al. "Cryo-EM structure of an antibody that neutralizes dengue virus type 2 by locking E protein dimers" Science, 349(6243):88-91 (2015).
Fibriansah et al. "A highly potent human antibody neutralizes dengue virus serotype 3 by binding across three surface proteins" Nature Communications, 6(6341):1-10 (2015).
International Preliminary Report on Patentability corresponding to International Patent Application No. PCT/US2016/052706 (6 pages) (dated Apr. 19, 2018).
Metz et al. "Display of quaternary epitopes recognized by dengue virus neutralizing antibodies" Abstract presented at the International Symposium on Flaviviruses: Structure and Immunity (1 page) Vienna, Austria, Oct. 8-10, 2015.
Metz et al. "In Vitro Assembly and Stabilization of Dengue and Zika Virus Envelope Protein Homo-Dimers" Scientific Reports, 7(4524):1-8 (2017).
Rouvinski et al. "Recognition determinants of broadly neutralizing human antibodies against dengue viruses" Nature, 520:109-113 (2015).
Wang et al. "PrM- and Cell-Binding Domains of the Dengue Virus E Protein" Journal of Virology, 73(3):2547-2551 (1999).

* cited by examiner

*Primary Examiner* — Shanon A. Foley
(74) *Attorney, Agent, or Firm* — Myers Bigel, P.A.

(57) ABSTRACT

The present invention provides compositions directed to recombinant flavivirus E glycoprotein ectodomain dimers for use in diagnostic and immunotherapeutic methods.

6 Claims, 17 Drawing Sheets

Specification includes a Sequence Listing.

SEQUENCE LISTING

<160> NUMBER OF SEQ ID NOS: 5

<210> SEQ ID NO 1
<211> LENGTH: 395
<212> TYPE: PRT
<213> ORGANISM: Artificial
<220> FEATURE:
<223> OTHER INFORMATION: denv3

<400> SEQUENCE: 1

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Gln Lys Thr
            35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Val Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

```
Glu Thr Pro Thr Trp Asn Arg Lys Glu Leu Leu Val Thr Phe Lys Asn
225                 230                 235                 240

Ala His Ala Lys Lys Gln Glu Val Val Leu Gly Ser Gln Glu Gly
            245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
            275                 280                 285

Lys Leu Glu Leu Lys Gly Met Ser Tyr Ala Met Cys Leu Asn Thr Phe
            290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
            355                 360                 365

Pro Pro Phe Gly Glu Ser Asn Ile Val Ile Gly Ile Gly Asp Lys Ala
370                 375                 380

Leu Lys Ile Asn Trp Tyr Lys Lys Gly Ser Ser
385                 390                 395

<210> SEQ ID NO 2
<211> LENGTH: 397
<212> TYPE: PRT
<213> ORGANISM: Artificial
<220> FEATURE:
<223> OTHER INFORMATION: denv1

<400> SEQUENCE: 2

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190
```

```
Phe Asn Glu Met Val Leu Leu Thr Met Glu Lys Lys Ser Trp Leu Val
            195                 200                 205
His Lys Gln Trp Phe Leu Asp Leu Pro Leu Pro Trp Thr Ser Gly Ala
210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
            245                 250                 255
Glu Gly Ala Met His Thr Ala Leu Thr Gly Ala Thr Glu Ile Gln Thr
            260                 265                 270
Ser Gly Thr Thr Thr Ile Phe Ala Gly His Leu Lys Cys Arg Leu Lys
            275                 280                 285
Met Asp Lys Leu Thr Leu Lys Gly Met Ser Tyr Val Met Cys Thr Gly
290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
            325                 330                 335
Phe Ser Ser Gln Asp Glu Lys Gly Val Thr Gln Asn Gly Arg Leu Ile
            340                 345                 350
Thr Ala Asn Pro Ile Val Thr Asp Lys Glu Lys Pro Val Asn Ile Glu
            355                 360                 365
Ala Glu Pro Pro Phe Gly Glu Ser Tyr Ile Val Val Gly Ala Gly Glu
            370                 375                 380
Lys Ala Leu Lys Leu Ser Trp Phe Lys Lys Gly Ser Ser
385                 390                 395

<210> SEQ ID NO 3
<211> LENGTH: 397
<212> TYPE: PRT
<213> ORGANISM: Artificial
<220> FEATURE:
<223> OTHER INFORMATION: denv2

<400> SEQUENCE: 3

Met Arg Cys Ile Gly Ile Ser Asn Arg Asp Phe Val Glu Gly Val Ser
1               5                   10                  15
Gly Gly Ser Trp Val Asp Ile Val Leu Glu His Gly Ser Cys Val Thr
            20                  25                  30
Thr Met Ala Lys Asn Lys Pro Thr Leu Asp Phe Glu Leu Ile Lys Thr
        35                  40                  45
Glu Ala Lys Gln Pro Ala Thr Leu Arg Lys Tyr Cys Ile Glu Ala Lys
    50                  55                  60
Leu Thr Asn Thr Thr Thr Glu Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Gly Leu Phe Gly Lys Gly Gly
            100                 105                 110
Ile Val Thr Cys Ala Met Phe Thr Cys Lys Lys Asn Met Glu Gly Lys
        115                 120                 125
Val Val Gln Pro Glu Asn Leu Glu Tyr Thr Ile Val Val Thr Pro His
    130                 135                 140
Ser Gly Glu Glu His Ala Val Gly Asn Asp Thr Gly Lys His Gly Lys
145                 150                 155                 160
```

```
Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Asp Pro
370                 375                 380

Gly Gln Leu Lys Leu Asn Trp Phe Lys Lys Gly Ser Ser
385                 390                 395

<210> SEQ ID NO 4
<211> LENGTH: 397
<212> TYPE: PRT
<213> ORGANISM: Artificial
<220> FEATURE:
<223> OTHER INFORMATION: denv4

<400> SEQUENCE: 4

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Leu Cys Ser Gly Lys Ile Thr Gly Asn
        115                 120                 125
```

Leu Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Arg Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Ser Thr Asn Ser Val Thr Asn Ile Glu
        355                 360                 365

Leu Glu Pro Pro Phe Gly Asp Ser Tyr Ile Val Ile Gly Val Gly Asp
    370                 375                 380

Ser Ala Leu Thr Leu His Trp Phe Arg Lys Gly Ser Ser
385                 390                 395

<210> SEQ ID NO 5
<211> LENGTH: 702
<212> TYPE: PRT
<213> ORGANISM: Artificial
<220> FEATURE:
<223> OTHER INFORMATION: DV2

<400> SEQUENCE: 5

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

```
Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
            115                 120                 125

Ser Arg Gln Glu Lys Gly Lys Ser Leu Leu Phe Lys Thr Glu Asp Gly
            130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
        450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510
```

-continued

```
Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe
    690                 695                 700
```

US 10,772,948 B2

METHODS AND COMPOSITIONS FOR DENGUE VIRUS VACCINES AND DIAGNOSTICS

STATEMENT OF PRIORITY

This application claims the benefit, under 35 U.S.C. § 119(e), of U.S. Provisional Application No. 62/238,496, filed Oct. 7, 2015, the entire contents of which are incorporated by reference herein.

STATEMENT OF GOVERNMENT SUPPORT

This application is a 35 U.S.C. § 371 national phase application of International Application Serial No. PCT/US2016/052706, filed Sep. 20, 2016, which claims the benefit, under 35 U.S.C. § 119(e), of U.S. Provisional Application No. 62/238,496, filed Oct. 7, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-762 ST25.txt, 20,321 bytes in size, generated on Apr. 3, 2018 and filed via EFS-Web, is provided in lieu of a paper copy. This Sequence Listing is incorporated by reference into the specification for its disclosures.

FIELD OF THE INVENTION

The present invention is directed to flavivirus vaccines that induce neutralizing antibodies.

BACKGROUND OF THE INVENTION

Dengue virus (DENV) is the causative agent of dengue fever and dengue hemorrhagic fever. DENV and its mosquito vectors are widely distributed in tropical and subtropical regions and the disease is endemic in over 100 countries. There are no approved vaccines for dengue.

Dengue virus induced antibody responses are mainly targeted against the envelope (E) protein. Many non-neutralizing antibodies are cross-reactive between the 4 different DENV serotypes (DENV-1-4) and recognize specific epitopes on E that do not attribute to the protection against DENV infections. Highly potent neutralizing antibodies are often targeted against epitopes that require higher order quaternary protein structures that are assembled and displayed on intact virions only. Between serotypes, the neutralizing epitopes differ in structure, complexity and location. These serotype specific neutralizing antibodies render protection against subsequent virus infections of the same serotype.

Leading dengue vaccines are based on tetravalent attenuated live dengue virus formulations. A recent human efficacy study with a live vaccine failed to generate balanced protective immune responses to all 4 serotypes. Moreover, some vaccinated people appear to have higher risk of developing disease after natural infections. Vaccines based on recombinant dengue E proteins are likely to be safer and easier to balance across the 4 serotypes. However, as recombinant proteins are secreted as monomers, the key quaternary epitopes targeted by human antibodies are not displayed on recombinant proteins.

The present invention overcomes previous shortcomings in the art by providing compositions and methods directed to reconstructing complex quaternary neutralizing epitopes on artificial surfaces for use in diagnostics and vaccines.

SUMMARY OF THE INVENTION

Figure 1:
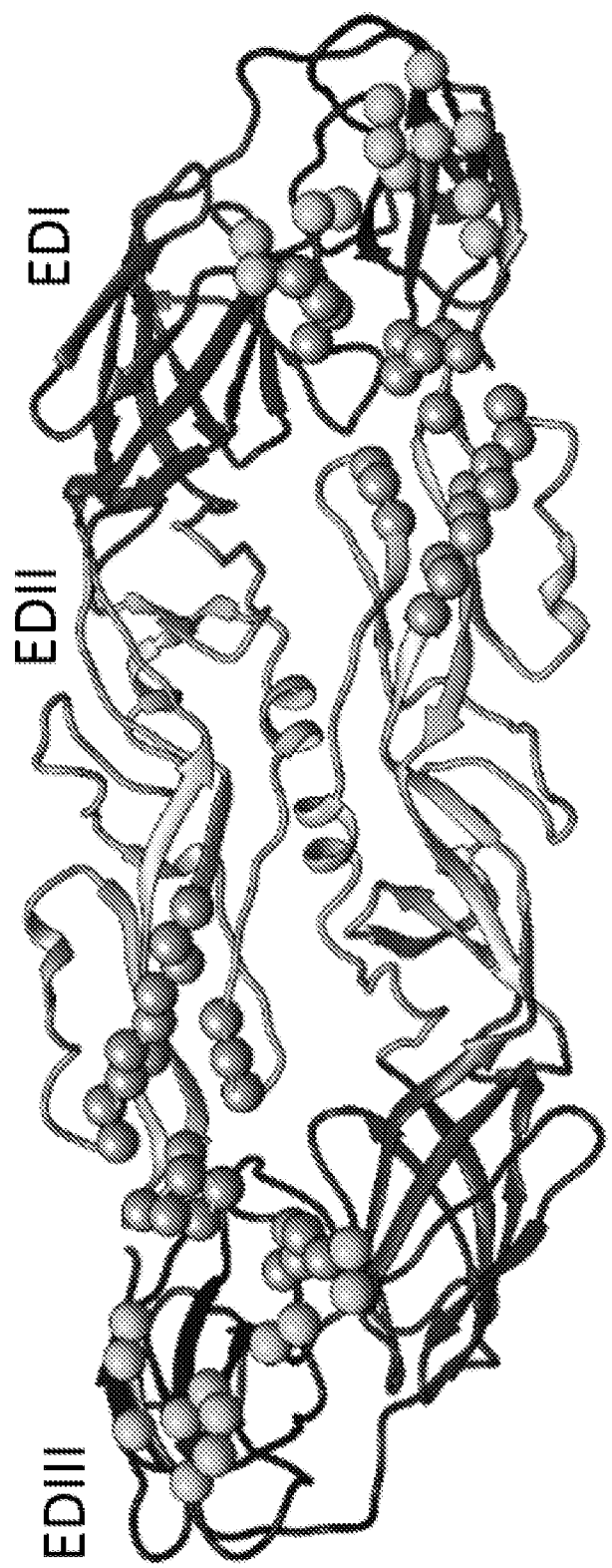
FIG. 1. Protein structure of the DENV-2 E protein dimer. Indicated are E-domain (ED)I, EDII and EDIII. The residues that interact with the heavy and light chains of 2D22 are indicated in spheres.

In one aspect, the present invention provides a method of producing a recombinant soluble flavivirus E ectodomain dimer, comprising: a) preparing a first recombinant soluble monomeric flavivirus E ectodomain comprising a functional first linking moiety at one terminus; b) contacting the first ectodomain with a second linking moiety that associates with the first linking moiety, wherein the second linking moiety is attached to a solid substrate, thereby attaching the ectodomain to the solid substrate in a specific orientation; c) contacting the first ectodomain attached to the solid substrate with a second recombinant monomeric flavivirus E ectodomain lacking a functional first linking moiety under conditions whereby dimerization of the first ectodomain and second ectodomain can occur; d) detaching the recombinant soluble flavivirus E ectodomain dimers from the solid substrate; and e) collecting the recombinant soluble flavivirus E ectodomain dimers.

In an additional aspect, the present invention provides a method of producing a recombinant flavivirus E ectodomain dimer attached to a solid substrate, comprising: a) preparing a first recombinant monomeric flavivirus E ectodomain comprising a functional first linking moiety at one terminus; b) contacting the first ectodomain with a second linking moiety that associates with the first linking moiety, wherein the second linking moiety is attached to a carrier, thereby attaching the ectodomain to the solid substrate in a specific orientation; and c) contacting the first ectodomain attached to the carrier with a second recombinant monomeric flavivirus E ectodomain lacking a functional first linking moiety under conditions whereby dimerization of the first ectodomain and second ectodomain can occur.

As a further aspect, the present invention provides a method of identifying an antibody that recognizes a quaternary epitope spanning both monomers of a flavivirus E protein ectodomain dimer, comprising: a) preparing a first recombinant soluble monomeric flavivirus E ectodomain comprising a functional first linking moiety at one terminus; b) contacting the first ectodomain with a second linking moiety that associates with the first linking moiety, wherein the second linking moiety is attached to a solid substrate, thereby attaching the ectodomain to the solid substrate in a specific orientation; c) contacting the first ectodomain attached to the solid substrate with a second recombinant monomeric flavivirus E ectodomain lacking a functional first linking moiety under conditions whereby dimerization of the first ectodomain and second ectodomain can occur; d) contacting the sample with the dimerized ectodomain of (c) under conditions whereby formation of antibody/antigen complexes can occur; and e) detecting formation of antibody/antigen complexes, thereby identifying an antibody that recognizes a quaternary epitope spanning both monomers of the flavivirus E protein ectodomain dimer.

In additional embodiments, the present invention provides a method of producing an immune response to a flavivirus in a subject, comprising administering to the subject an effective amount of the dimer and/or any of the compositions of this invention, in any combination.

Also provided herein is a method of treating a flavivirus infection in a subject, comprising administering to the subject an effective amount of the dimer and/or any of the compositions of this invention, in any combination.

Further provided herein is a method of preventing a flavivirus infection in a subject, comprising administering to the subject an effective amount of the dimer and/or any of the compositions of this invention, in any combination.

Also provided herein is a method of protecting a subject from the effects of flavivirus infection, comprising administering to the subject an effective amount of the dimer and/or any of the compositions of this invention, in any combination.

The present invention further provides the E glycoprotein ectodomain dimer of this invention and/or any of the compositions of this invention for use in the manufacture of a medicament for producing an immune response to a flavivirus in a subject, for treating a flavivirus infection in a subject in need thereof, for preventing a flavivirus infection in a subject and/or for protecting a subject from the effects of flavivirus infection.

Also provided herein is the use of the E glycoprotein ectodomain dimer of this invention of this invention and/or any of the compositions of this invention for use in producing an immune response to a flavivirus in a subject, in treating a flavivirus infection in a subject in need thereof, in preventing a flavivirus infection in a subject and/or in protecting a subject from the effects of flavivirus infection.

DETAILED DESCRIPTION OF THE INVENTION

The present invention is based on the unexpected discovery that complex quaternary neutralizing epitopes of flaviviruses can be constructed on a solid substrate. Thus, in one embodiment, the present invention provides a method of producing a recombinant soluble flavivirus E ectodomain dimer, comprising: a) preparing a first recombinant soluble monomeric flavivirus E ectodomain comprising a functional first linking moiety at one terminus; b) contacting the first ectodomain with a second linking moiety that associates with the first linking moiety, wherein the second linking moiety is attached to a solid substrate, thereby attaching the ectodomain to the solid substrate in a specific orientation; c) contacting the first ectodomain attached to the solid substrate with a second recombinant monomeric flavivirus E ectodomain lacking a functional first linking moiety under conditions whereby dimerization of the first ectodomain and second ectodomain can occur; d) detaching the recombinant soluble flavivirus E ectodomain dimers from the solid substrate; and e) collecting the recombinant soluble flavivirus E ectodomain dimers.

In an additional aspect, the present invention provides a method of producing a recombinant flavivirus E ectodomain dimer attached to a solid substrate, comprising: a) preparing a first recombinant monomeric flavivirus E ectodomain comprising a functional first linking moiety at one terminus; b) contacting the first ectodomain with a second linking moiety that associates with the first linking moiety, wherein the second linking moiety is attached to a carrier, thereby attaching the ectodomain to the solid substrate in a specific orientation; and c) contacting the first ectodomain attached to the carrier with a second recombinant monomeric flavivirus E ectodomain lacking a functional first linking moiety under conditions whereby dimerization of the first ectodomain and second ectodomain can occur.

Furthermore, the present invention provides a method of identifying an antibody in a sample that recognizes a quaternary epitope spanning both monomers of a flavivirus E protein ectodomain dimer, comprising: a) preparing a first recombinant soluble monomeric flavivirus E ectodomain comprising a functional first linking moiety at one terminus; b) contacting the first ectodomain with a second linking moiety that associates with the first linking moiety, wherein the second linking moiety is attached to, a solid substrate, thereby attaching the ectodomain to the solid substrate in a specific orientation; c) contacting the first ectodomain attached to the solid substrate with a second recombinant monomeric flavivirus E ectodomain lacking a functional first linking moiety under conditions whereby dimerization of the first ectodomain and second ectodomain can occur; d) contacting the sample with the dimerized ectodomain of (c) under conditions whereby formation of antibody/antigen complexes can occur; and e) detecting formation of antibody/antigen complexes, thereby identifying an antibody that recognizes a quaternary epitope spanning both monomers of the flavivirus E protein ectodomain dimer.

In embodiments of this invention that employ a method of identifying an antibody that recognizes a quaternary epitope spanning multiple monomers of a flavivirus E protein ectodomain dimer, additional steps can be employed prior to, concurrent with and/or after the method in which an antibody in the sample that recognizes an epitope that is not a quaternary epitope can be detected. As one nonlimiting example, a portion of the sample can be contacted with a flavivirus E ectodomain monomer under conditions whereby an antigen/antibody complex can form and steps to detect any such antigen/antibody complexes can be carried out.

As another example, a blockade of binding assay can be carried out, in which a first portion of the sample is contacted with a dimer of this invention under conditions whereby an antigen/antibody complex can form and a second portion of the sample can be contacted with a dimer of this invention after the dimer has been contacted with an antibody known to bind a quaternary epitope on the dimer. If an antigen/antibody complex formation is detected in the first portion of the sample but no antibody/antigen complex formation is detected in the second portion of the sample, the antibody involved in antigen/antibody complex formation in the first portion of the sample is identified as an antibody that recognizes a quaternary epitope spanning multiple monomers. As antibodies to quaternary epitopes neutralize dengue viruses, the ability to detect antibodies in clinical samples directed to these epitopes is useful for evaluating vaccines in clinical trials and predicting vaccine efficacy both at the individual and population level.

In some embodiments of this invention, the first linking moiety and second linking moiety, respectively, can be but are not limited to 1) a histidine tag (HIS) and $Ni^{2+}$, respectively; 2) biotin and avidin, respectively; and 3) a primary α-helix and a secondary α-helix, respectively. Additional nonlimiting examples of linking moieties that can be used in this invention include a HA tag or other epitope tag as would be well known in the art as a first linking moiety and a Fab fragment of an antibody specific to the epitope tag as the second linking moiety, as well as a chemically reactive group at the C-terminus of E protein ectodomain as a first linking moiety and a second linking moiety that is chemically reactive with the first linking moiety. These linking moieties can associate with one another using specific amine or sulfhydryl chemistry as would be well known in the art.

In some embodiments of this invention, the flavivirus is a dengue virus. There are four serotypes of dengue virus (DENV-1, DENV-2, DENV-3 and DENV-4). Within each serotype there are a number of different strains or genotypes. The dengue virus antigens and epitopes of the invention can be derived from any dengue virus, including all serotypes, strains and genotypes, now known or later identified.

In some embodiments of the invention, the dengue virus is UNC1017 strain (DENV-1), West Pacific 74 strain (DENV-1), S16803 strain (DEN2), UNC2005 strain (DENV-2), UNC3001 strain (DENV-3), UNC3043 (DENV-3 strain 059.AP-2 from Philippines, 1984), UNC3009 strain (DENV-3, D2863, Sri Lanka 1989), UNC3066 (DEN3, strain 1342 from Puerto Rico 1977), CH53489 strain (DENV-3), UNC4019 strain (DENV-4), or TVP-360 (DENV-4).

Nonlimiting examples of other flaviviruses that can be used in this invention include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652), tick-borne encephalitis virus (TBEV) (e.g., GenBank® Database Accession No. P14336) and any other flavivirus now known or later identified.

The present invention further provides a recombinant flavivirus E ectodomain dimer produced by the method of this invention, as well as a recombinant flavivirus E ectodomain dimer attached to a solid substrate. In some embodiments, the recombinant flavivirus E ectodomain dimer will have the first linking moiety attached and in some embodiments, this first linking moiety is removed, e.g., when the flavivirus ectodomain dimer is to be administered to a subject and the first linking moiety is not appropriate (e.g., biologically safe) for administration to the subject. In some embodiments, the flavivirus ectodomain dimer of this invention can have the first linking moiety attached even in embodiments in which the dimer is administered to a subject, if the first linking moiety is biologically compatible with the subject.

The term "flavivirus E ectodomain" refers to all of the amino acid sequence that is outside the virus and does not include portions of the protein that are embedded in the membrane or inside the virus. In the case of dengue virus E ectodomains, there are some helical segments that are outside the virus and loosely associated with the viral membrane, which are typically not included in the soluble protein referred to as the ectodomain. The E ectodomain typically comprises about 400 amino acids, typically numbered as 1 to 400 in the amino acid sequence of the flavivirus E protein.

A solid substrate of this invention can be any solid surface to which one or more flavivirus E ectodomain monomers can attach in an orientation that allows for dimer formation according to the methods described herein. In some embodiments, the solid substrate can be, but is not limited to a plate, resin, dish, slide, well, etc., as would be commonly used in an immunoassay or any other type of assay or reaction.

In some embodiments of this invention, the solid substrate can be any type of carrier that has a surface to which one or more flavivirus E ectodomain monomers can attach in an orientation that allows for dimer formation according to the methods described herein. In some embodiments, the solid substrate can be a microparticle or nanoparticle.

Exemplary types of nanoparticles of this invention include but are not limited to, polymer nanoparticles such as PLGA-based, PLA-based, polysaccharide-based (dextran, cyclodextrin, chitosan, heparin), dendrimer, hydrogel; lipid-based nanoparticles such as lipid nanoparticles, lipid hybrid nanoparticles, liposomes, micelles; inorganics-based nanoparticles such as superparamagnetic iron oxide nanoparticles, metal nanoparticles, platin nanoparticles, calcium phosphate nanoparticles, quantum dots; carbon-based nanoparticles such as fullerenes, carbon nanotubes; and protein-based complexes with nanoscales.

Types of microparticles of this invention include but are not limited to particles with sizes at micrometer scale that are polymer microparticles including but not limited to, PLGA-based, PLA-based, polysaccharide-based (dextran, cyclodextrin, chitosan, heparin), dendrimer, hydrogel; lipid-based microparticles such as lipid microparticles, micelles;

inorganics-based microparticles such as superparamagnetic iron oxide microparticles, platin microparticles and the like as are known in the art.

As used herein, the terms "nanoparticle" and "nanosphere" describe a polymeric particle or sphere in the nanometer size range. The term microparticle" or "microsphere" as used herein describes a particle or sphere in the micrometer size range. Both types of particles or spheres can be used as carriers of this invention.

A nanoparticle or nanosphere of this invention can have a diameter of 100 nm or less (e.g., in a range from about 1 nm to about 100 nm). In some embodiments, a particle with dimensions more than 100 nm can still be called a nanoparticle. Thus, an upper range for nanoparticles can be about 500 nm. A microparticle or microsphere of this invention can have a diameter of about 0.5 micrometers to about 100 micrometers.

In some embodiments of a nanoparticle or microparticle of this invention, the dimer or multiplicity of dimers is attached to the exterior surface using hydrophobic noncovalent interaction or covalent linkage based on amine/carboxylate chemistry, thiol/maleimide chemistry, and disulfide chemistry. For hydrophobic noncovalent interaction, unmodified monomer and/or dimer can be directly absorbed on the surface of particles. Alternatively, the monomer or dimer can be first chemically or enzymatically modified by conjugation with a fatty acid (i.e., lauric acid, myristic acid, palmitic acid, stearic acid, arachidic acid, oleic acid, etc.), whose long carbon chain allows for tight and strong hydrophobic interaction with or insertion into the surface of particles. For covalent linkage, the functional groups on the surface of particles are first derivatized or activated to introduce activated ester, activated disulfide, or maleimide, followed by reaction with the monomer and/or dimer of this invention.

In some embodiments, a particle of this invention can comprise a polymer that can be PLGA-based, PLA-based, and/or polysaccharide-based (dextran, cyclodextrin, chitosan, heparin etc.); a dendrimer; a hydrogel; a lipid base; a lipid hybrid base; a liposome; a micelle; an inorganic base such as, e.g., superparamagnetic iron oxide, metal, platin, calcium phosphate; a quantum dot; a carbon base, such as, e.g., a fullerene, a carbon nanotube; and a protein-based complex with nanoscales.

In certain embodiments, liposomes may also be employed with the monomers and/or dimers of this invention. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via at least four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

In some embodiments of this invention, the solid substrate can be a nanocapsule. Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

In still further embodiments of the invention, the present invention provides peptide mimitopes (see, Meloen et al. (2000) *J. Mol. Recognit.* 13, 352-359) that mimic the individual and conformational epitopes of the E glycoproteins of the invention. Mimitopes may be identified using any technique known in the art, such as by surface stimulation, random peptide libraries or phage display libraries, using an antibody or antibodies to the individual and conformational epitopes of the E glycoproteins of the invention.

The present invention also contemplates the production and use of the dimers of this invention as higher order structures (e.g., three dimers associated with one another to form a "raft") for use in the methods of this invention. Such higher order structures comprise quaternary epitopes made up of amino acid residues from multiple dimers and can be used to generate an immune response specific to these complex quaternary epitopes. Tables 1-4 provided herein show the particular amino acid residues from respective dimers that have been identified as part of the quaternary epitope (amino acid residue numbering is based on the reference amino acid sequences provided herein) (Fibriansah et al. "DENGUE VIRUS. Cryo-EM structure of an antibody that neutralizes dengue virus type 2 by locking E protein dimers" *Science* 349(6243):88-91 (2015); Fibriansah et al. "A highly potent human antibody neutralizes dengue virus serotype 3 by binding across three surface proteins" *Nat Commun.* 6:6341 (2015); Fibriansah et al. "A potent anti-dengue human antibody preferentially recognizes the conformation of E protein monomers assembled on the virus surface" *EMBO Mol Med.* 6(3):358-71 (2014)).

The invention further provides a nucleic acid molecule (e.g., isolated nucleic acid) encoding an ectodomain monomer and/or other polypeptide or peptide of this invention. Also provided are vectors encoding the nucleic acid molecules of the invention.

Also provided are cells comprising the monomers, dimers, polypeptides, peptides and/or nucleic acid molecules of this invention.

In additional embodiments, the present invention provides immunogenic compositions comprising the dimers, vectors, nucleic acid molecules, polypeptides and/or any of the compositions of the invention. In some embodiments, the immunogenic composition can be monovalent. In some embodiments, the immunogenic composition is multivalent (e.g., bivalent, trivalent, tetravalent) for dengue virus serotypes DENV-1, DENV-2, DENV-3 and/or DENV-4 in any combination.

The present invention further provides a method of producing an immune response to a flavivirus in a subject, comprising administering to the subject an effective amount of the dimer of this invention and/or any of the compositions of this invention, in any combination.

Furthermore, the present invention provides a method of treating a flavivirus infection in a subject, comprising administering to the subject an effective amount of the dimer of this invention and/or any of the compositions of this invention, in any combination.

Additionally provided herein is a method of preventing a flavivirus infection in a subject, comprising administering to the subject an effective amount of the dimer of this invention and/or any of the compositions of this invention, in any combination.

A method is also provided herein, of protecting a subject from the effects of flavivirus infection, comprising administering to the subject an effective amount of the dimer of this invention and/or any of the compositions of this invention, in any combination.

Further, it is contemplated that the present invention can advantageously be practiced to induce an immune response against one, two, three or all four of DENV-1, DENV-2, DENV-3 and DENV-4 serotypes. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to deleterious effects, such as dengue hemorrhagic fever.

In embodiments of the invention, an "immunogenically active fragment" of a flavivirus E protein ectodomain comprises, consists essentially of or consists of at least about 200, 275, 300, 325, 350, 375, 380, 390 or 395 amino acids, optionally contiguous amino acids, and/or less than about 400, 410, 420, 430, 440 450 or 451 amino acids, optionally contiguous amino acids, including any combination in between the foregoing as long as the lower limit is less than the upper limit, and the "immunogenically active fragment" induces an immune response (e.g., IgG and/or IgA that react with the native antigen), optionally a protective immune response, against flavivirus in a host and induces the production of antibodies that specifically bind to one or more quaternary flavivirus epitopes as described herein.

The term "epitope" as used herein means a specific combination of amino acid residues that, when present in the proper conformation, provide a reactive site for an immune response, e.g., involving an antibody (e.g., B cell epitope) and/or T cell receptor (e.g., T cell epitope).

Portions of a given polypeptide that include a B-cell epitope can be identified using any number of epitope mapping techniques that are known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) Molec. Immunol. 23:709-715.

Similarly, conformational epitopes can be readily identified by determining spatial conformation of amino acids such as by, e.g., cryoelectron microscopy, x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other reagent and/or solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides and other compositions of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DENV-1, DENV-2, DENV-3 and DENV-4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

The term "dengue virus E protein domain I and domain II hinge region" and similar terms would be understood in the art to include the three-dimensional interface between domain I and II in the dengue virus E glycoprotein and, optionally, the adjacent amino acid residues. In addition, those skilled in the art will appreciate that certain amino acid residues in the hinge region may facilitate proper folding and presentation of the epitope, even if they do not form part of the epitope per se. In representative embodiments, the dengue virus E protein domain I and domain II hinge region comprises, consists essentially of, or consists of amino acid positions 47-59, 124-133, 199-222 and/or 206-228 of the E protein of dengue virus serotype 3 (DENV-3; e.g., GenBank® Database Accession No. JQ411814) or the corresponding positions of the E protein of other dengue virus serotypes as described herein.

The term "at least a portion of a dengue virus E protein domain III" and similar terms refer to those portions of E protein domain III that form part of the epitope as well as those amino acid residues that facilitate proper folding and presentation of the epitope, even if they do not form part of the epitope per se. In representative embodiments, the dengue virus E protein domain III comprises, consists essentially of, or consists of amino acid positions 305-308, 323-325, 359-362 and/or 389-390 of the E protein of dengue virus serotype 3 or the corresponding positions of the E protein of other dengue virus serotypes as described herein.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of flavivirus infection.

"Effective amount" as used herein refers to an amount of a vector, nucleic acid, epitope, polypeptide, cell, particle, VLP, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing flavivirus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating flavivirus infection in a subject, whether against one or multiple strains, genotypes or serotypes of a flavivirus such as dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." (Herscowitz, *Immunophysiology: Cell Function and Cellular Interactions in Antibody Formation, in* IMMUNOLOGY: BASIC PROCESSES 117 (Joseph A. Bellanti ed., 1985)). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to flavivirus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by flavivirus. Alternatively, a subject according to the invention can also include a subject not previously known or suspected to be infected by flavivirus or in need of treatment for flavivirus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to a flavivirus of this invention.

A "subject in need" of the methods of the invention can be a subject known to be, or suspected of being, infected with, or at risk of being infected with, a flavivirus of this invention.

Pharmaceutical formulations (e g, immunogenic formulation) comprising the flavivirus epitopes, polypeptides, and/or other compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragments) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immuno-modulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., *Vaccine* 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutami-nyl-L-alanine-2-(1'-2'-dipalmitoyl-sn-glycero-3-hydroxy-phosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acy-lated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art. In embodiments of the invention, the adjuvant comprises an alphavirus adjuvant as described, for example in U.S. Pat. No. 7,862,829.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science and Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 µg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

Further, the composition of this invention can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

In embodiments of the invention, the dosage of a protein (e.g., a composition comprising a soluble dimer of this invention or a dimer linked to a carrier such as a nanoparticle) can be in a range of about $10^0$ to about $10^4$ micrograms+/−adjuvant.

EXAMPLES

Dengue virus (DENV) is the causative agent of dengue fever and dengue hemorrhagic fever. DENV and its mosquito vectors are widely distributed in tropical and subtropical regions and the disease is endemic in over 100 countries. Dengue vaccine development is challenging because of the need to protect against four antigenically distinct DENV serotypes and evidence that, under some conditions, specific immunity to the virus can enhance disease.

Recent studies have led to the identification of epitopes on the DENV envelope (E) protein targeted by human neutralizing antibodies. Some epitopes are preserved on the monomeric E protein, while other epitopes are complex and require the assembly of higher order E protein structures required for virion assembly. Here we describe studies to optimize the display of quaternary epitopes on artificial surfaces. The ectodomain of DENV E protein was expressed as a soluble recombinant protein (recE), which was secreted from cells. RecE was purified from the culture media and conjugated to a solid matrix. Using a large panel of human and mouse derived monoclonal antibodies, we confirmed that the conjugated protein was properly folded. Moreover, by adjusting factors such as pH, salinity and protein density, we optimized the display of quaternary structure neutralizing epitopes known to be critical for inducing protective antibody responses. These results have implications for developing novel subunit vaccines displaying quaternary epitopes from flaviviruses.

The studies described herein show that the ectodomain of DENV E protein was expressed as a soluble recombinant protein (RecE). RecE was purified and conjugated in a specific orientation to a solid matrix. The conjugated protein was exposed to a second load of highly concentrated RecE monomers under specific pH and salt conditions. Using a panel of human and mouse derived monoclonal antibodies, we confirmed that we can recreate the dimer-dependent quaternary epitopes found on wild type DENV-2 particles and that are known to be critical for inducing protective antibody responses. These findings show that complex quaternary structure epitopes displayed on the virus particle can be recreated using properly oriented recombinant proteins. The discovery has potential for developing dengue vaccines and diagnostics.

We isolated human monoclonal antibody (HMAb) 2D22 from a DENV-2 patient. This human antibody strongly neutralizes DENV2 in cell culture and is protective in an animal model of DENV-2 disease. HMab 2D22 binds to a quaternary epitope that requires dimerization of E protein (FIG. 1). Most neutralizing antibodies that develop after a natural DENV-2 infection also target the region on DENV-2 defined by the 2D22 epitope. Here we demonstrate how to self-assemble recombinantly expressed DENV-2 E proteins to form the quaternary epitope recognized by 2D22.

The DENV-2 E protein was expressed as a truncated soluble protein with a C-terminal histidine tag (sRecE) for purification purposes. The recombinant DENV-2 E ectodomain used in this study is composed of 395 amino acid residues spanning residues 1-300 (covering EDI and EDII) and residues 301-395 of EDIII. Recombinant E ectodomain of DENV-1, DENV-3 and DENV-4 serotypes are composed of the same stretch of amino acid residues specific to each serotype. The conformation of DENV-2 sRecE and presentation of known epitopes were analyzed by an enzyme-linked immunosorbent assay (ELISA) and panel of epitope mapped human and mouse MAbs.

Figure 2:
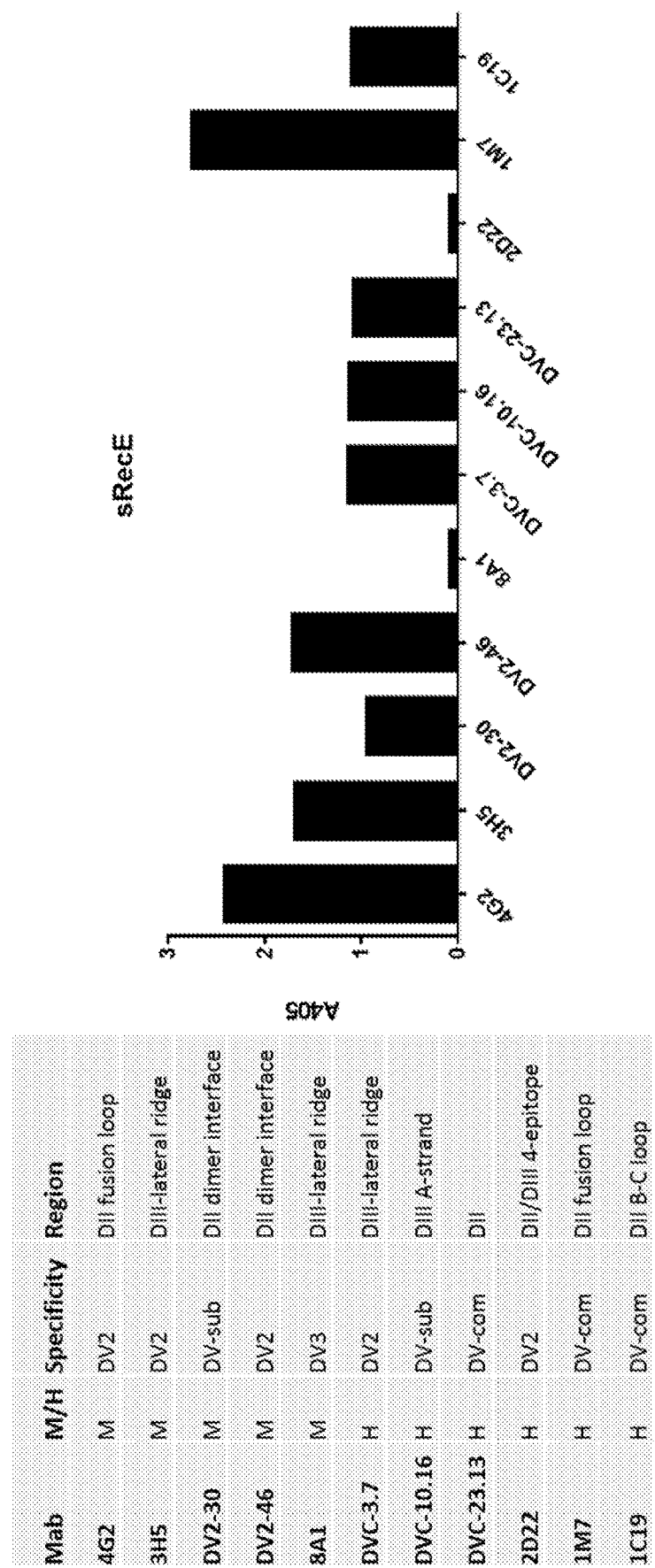
FIG. 2. Epitope screening of sRecE. 1 μg/well of RecE was loaded onto standard ELISA plates and subjected to a selection of mouse (M) and human (H) derived Mabs that recognize epitopes on different regions and of different complexities.

In initial experiments (FIG. 2), 1 µg/well sRecE was coated onto standard ELISA plates. This resulted in specific DENV-2 detection by the used antibodies. However, no 2D22 signal was detected, indicating that the complex quaternary 2D22 epitope was not recreated. This is most likely caused by the absence of correctly orientated RecE monomers, which are not able to form dimer structures.

Figure 3:
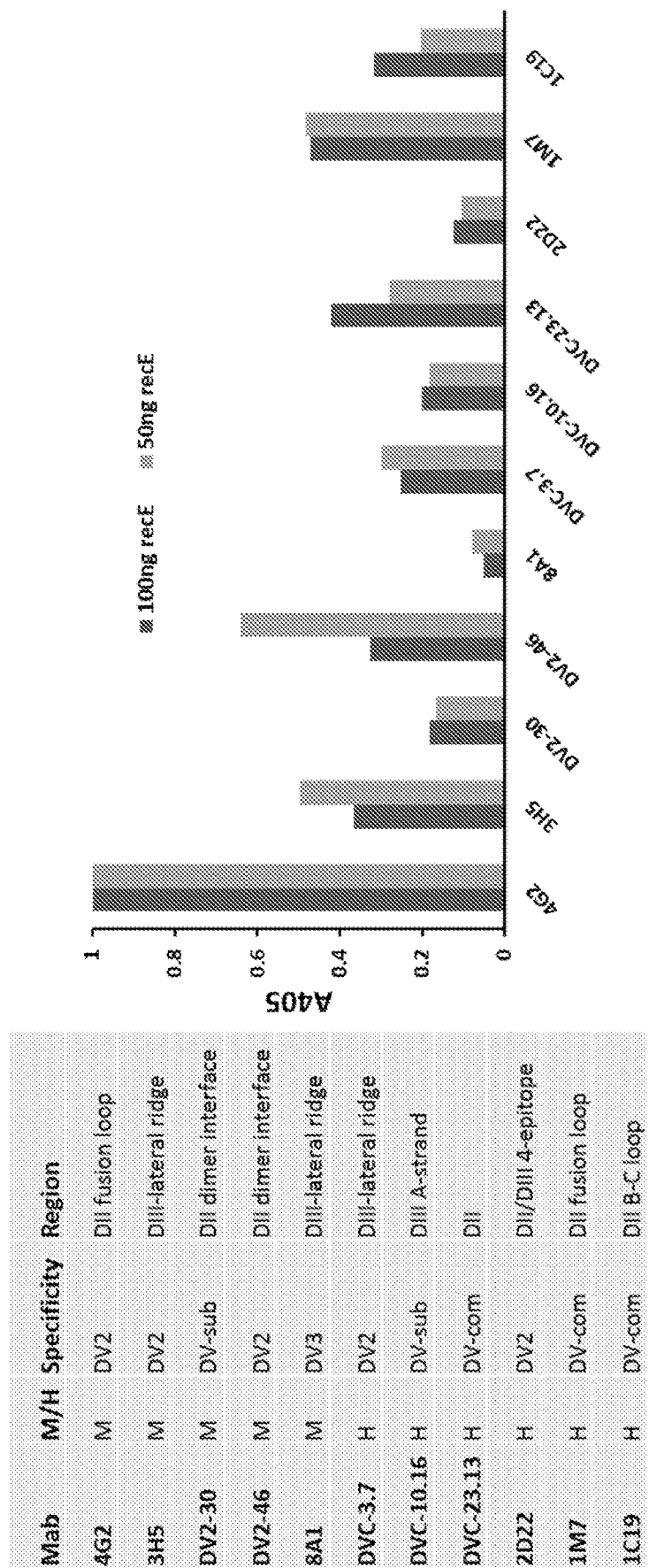
FIG. 3 Epitope screening of sRecE by $Ni^{2+}$-ELISA. Different concentrations of RecE (100 ng/well or 50 ng/well) were loaded onto $Ni^{2+}$-ELISA plate and subjected to a selection of mouse (M) and human (H) derived Mabs that recognize epitopes on different regions and of different complexities.

Next, $Ni^{2+}$-coated ELISA plates were used to capture sRecE is a specific orientation through interactions between the His-tail and free $Ni^{2+}$ groups. Bound RecE was subsequently exposed to a variety of human and mice derived DENV-2 specific and cross-reactive antibodies (FIG. 3). Results show that many epitopes present on wild type virus particles can be detected on the $Ni^{2+}$-bound RecE. In addition, we show that the 2D22 antibody was able to bind RecE poorly. The low 2D22 signal indicates that the dimer-dependent 2D22 epitope was poorly reconstructed by the binding of RecE to the $Ni^{2+}$ plate.

Figure 4:
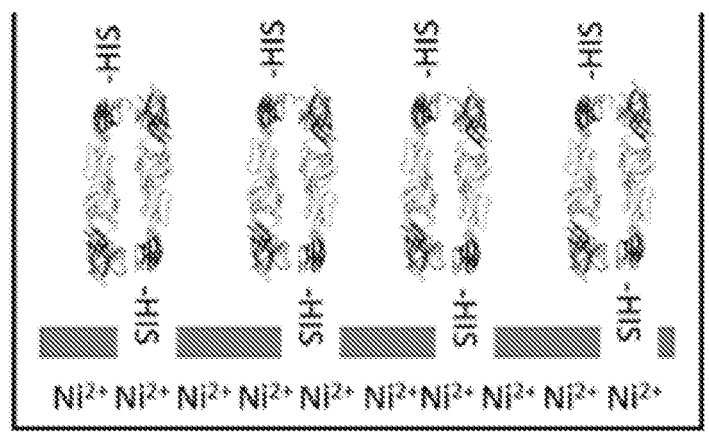
FIG. 4 $Ni^{2+}$-reload ELISA. A) sRecE is captured by free $Ni^{2+}$-groups on the ELISA plate. Remaining free groups are subsequently blocked and the bound RecE is subjected to a second load of RecE. The efficiency of dimer formation at different RecE concentrations is analyzed as the ratio (C) between the 4G2 and the 2D22 signals (B).
Figure 4:
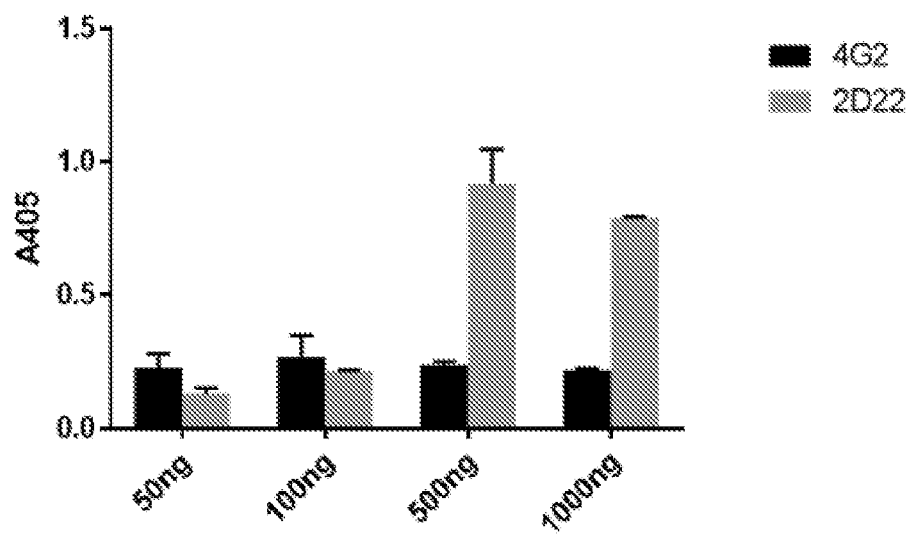
Figure 4:
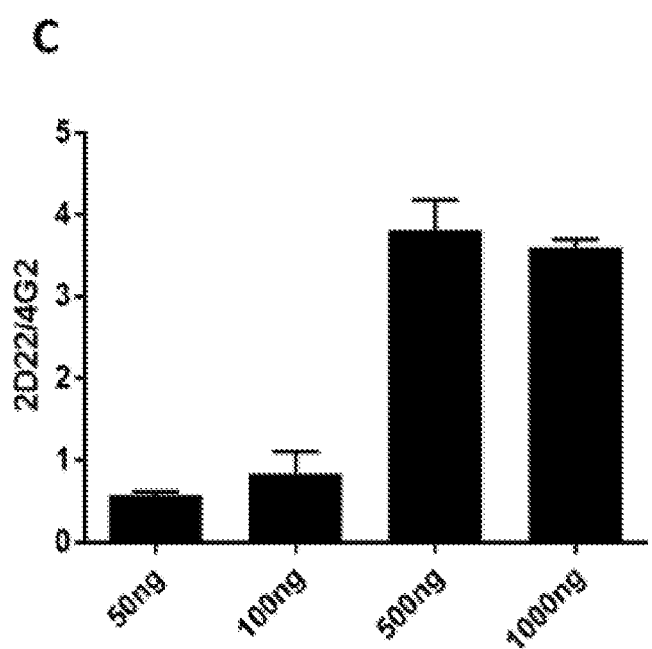

To further enhance the 2D22 signal, a new ELISA was designed (FIG. 4A) where sRecE was bound to free $Ni^{2+}$ and subsequently exposed to another load of sRecE. The primary sRecE monomer is immobilized in a specific conformation, so that the secondary sRecE is able to bind the immobilized RecE and form dimer structures required for 2D22 epitope formation. The increase of dimerization was analyzed by the ratio between 4G2 (a Mab that recognizes a monomeric epitope on the EDII fusion loop region) and 2D22 binding in similar conditions.

Initial results (FIG. 4B-C) show that a primary and secondary load of sRecE at low protein concentrations (50 and 100 ng/well) do not have any effect on dimerization. However, at higher protein concentrations (500 and 1000 ng/well), the 2D22 signal significantly increased compared to the 4G2 signal, showing the formation of RecE dimers.

Figure 5:
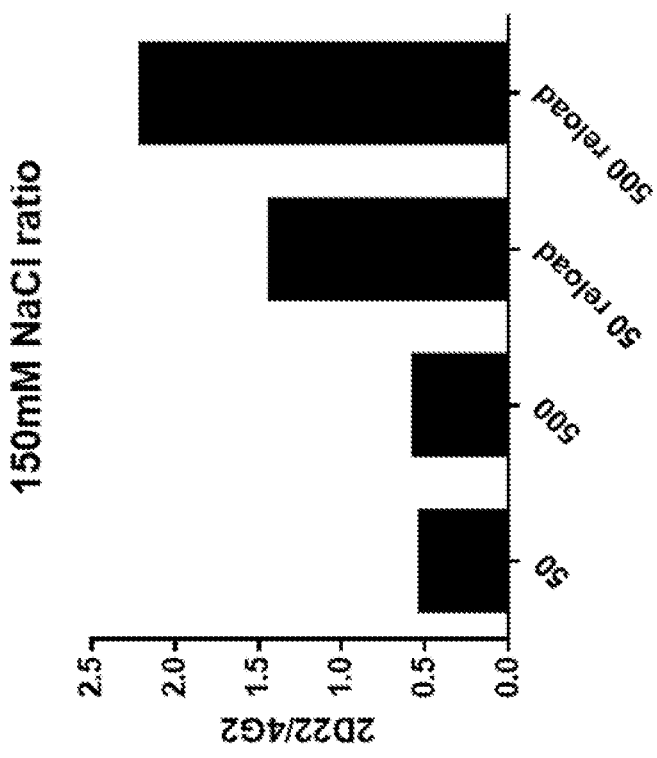
FIG. 5. The sRecE reload is essential for dimer formation. Low (50 ng/well) and high (500 ng/well) sRecE concentrations were loaded onto the $Ni^{2+}$-plates and reloaded with no or similar amounts of sRecE.
Figure 5:
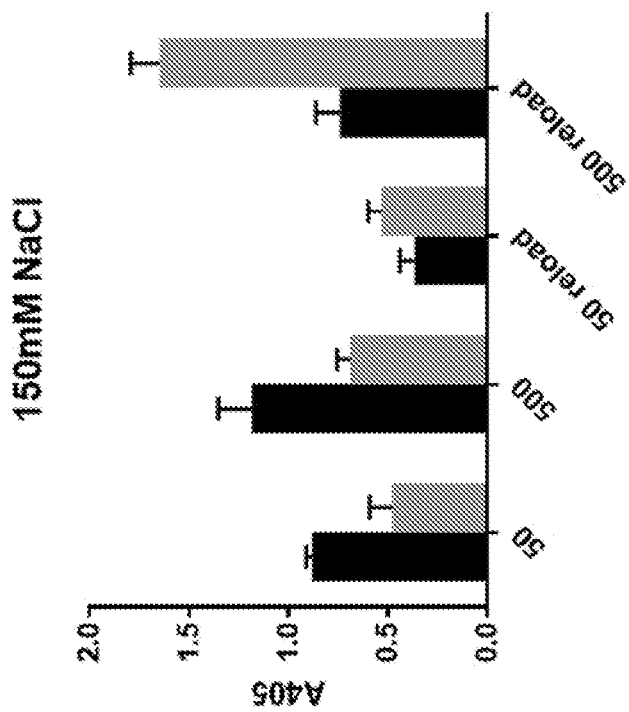

To determine if the reload step is essential in dimer formation, the experiment was repeated with and without a secondary sRecE reload at high and low protein concentrations (50 and 500 ng/well) (FIG. 5). Results show that the 2D22 signal only increases when the primary bound RecE is exposed to a reload. The dimerization effect was more potent at higher protein concentrations.

Figure 6:
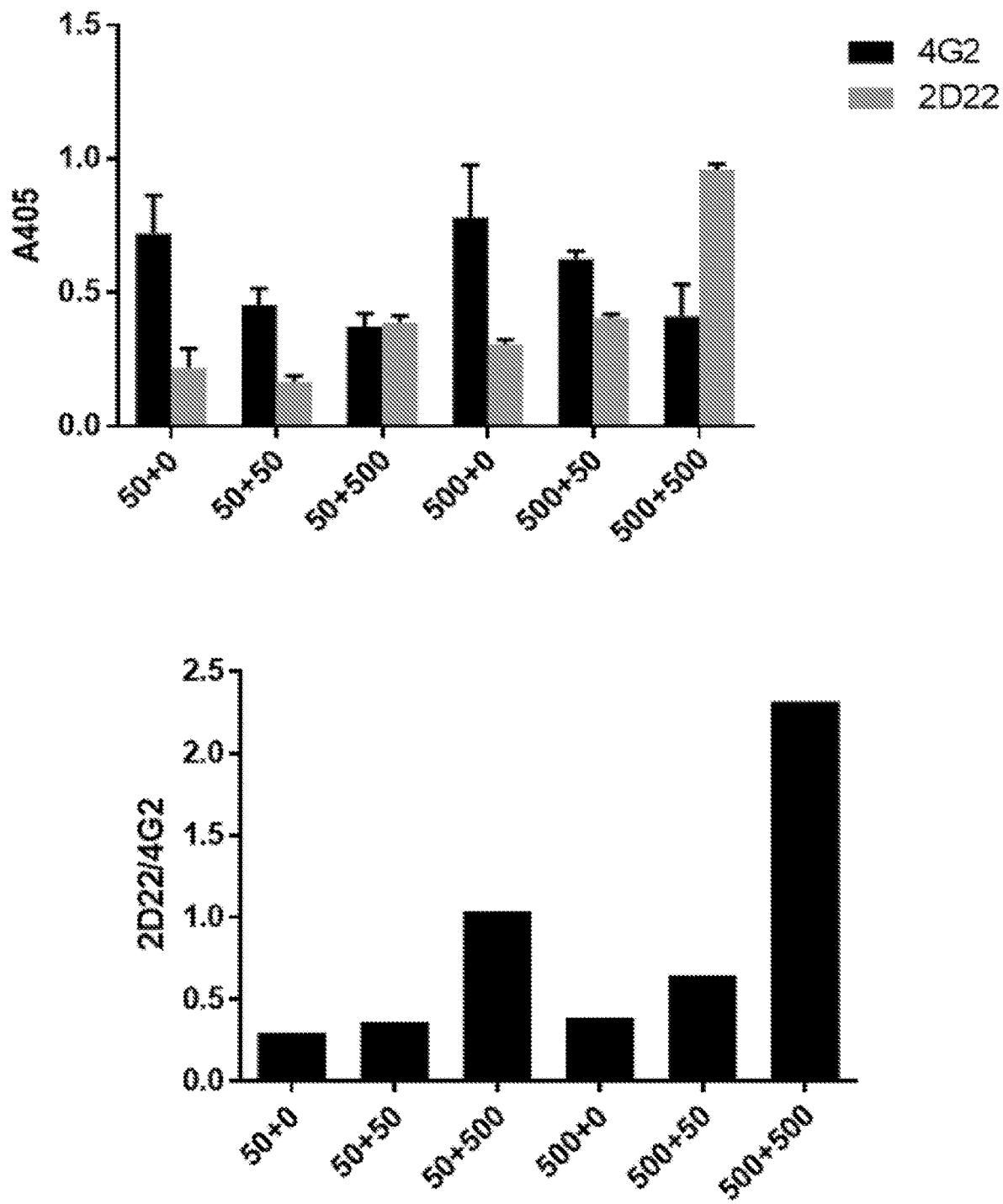
FIG. 6. High sRecE concentration during reload is most efficient for dimer formation. Low (50 ng/well) and high (500 ng/well) sRecE concentration were loaded onto the $Ni^{2+}$-plates and reloaded with 0, 50, or 500 ng/well of sRecE.

To examine whether the primary or secondary reload is limiting the dimerization efficiency, low and high concentrations (50 and 500 ng/well) of RecE were reloaded with 0, 50 and 500 ng/well of secondary sRecE (FIG. 6). This showed that the dimerization efficiency increases with increasing concentrations of secondary sRecE. The effect was most significant if 500 ng/ml of primary RecE is reloaded with 500 ng/well of secondary sRecE.

Figure 7:
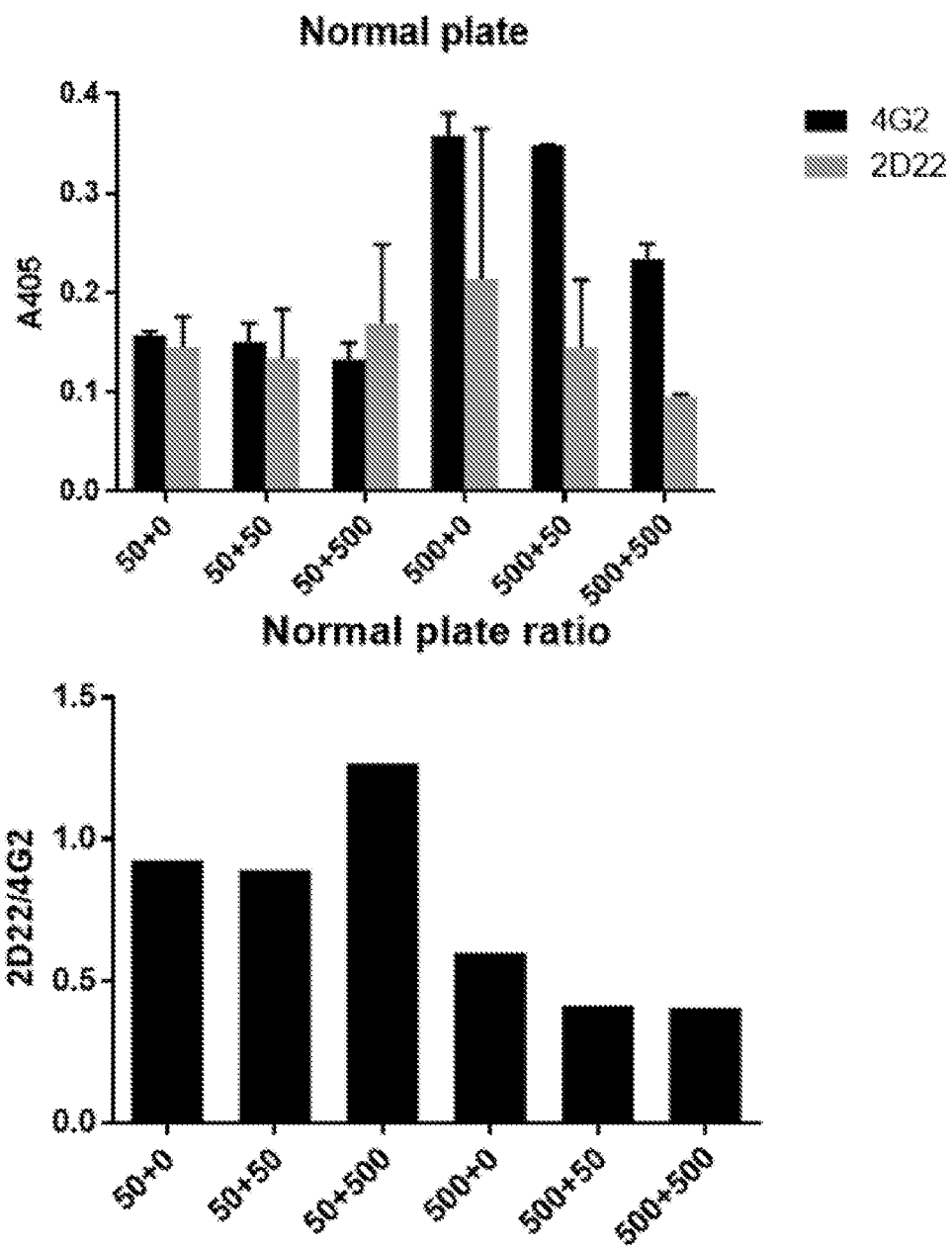
FIG. 7. Orientation of primary sRecE on Ni2+ plate is critical for in vitro dimer formation. Low (50 ng/well) and high (500 ng/well) sRecE concentration were loaded onto the $Ni^{2+}$-plates and regular ELISA plates. Next, the bound RecE was reloaded with 0, 50, or 500 ng/well of sRecE.
Figure 7:
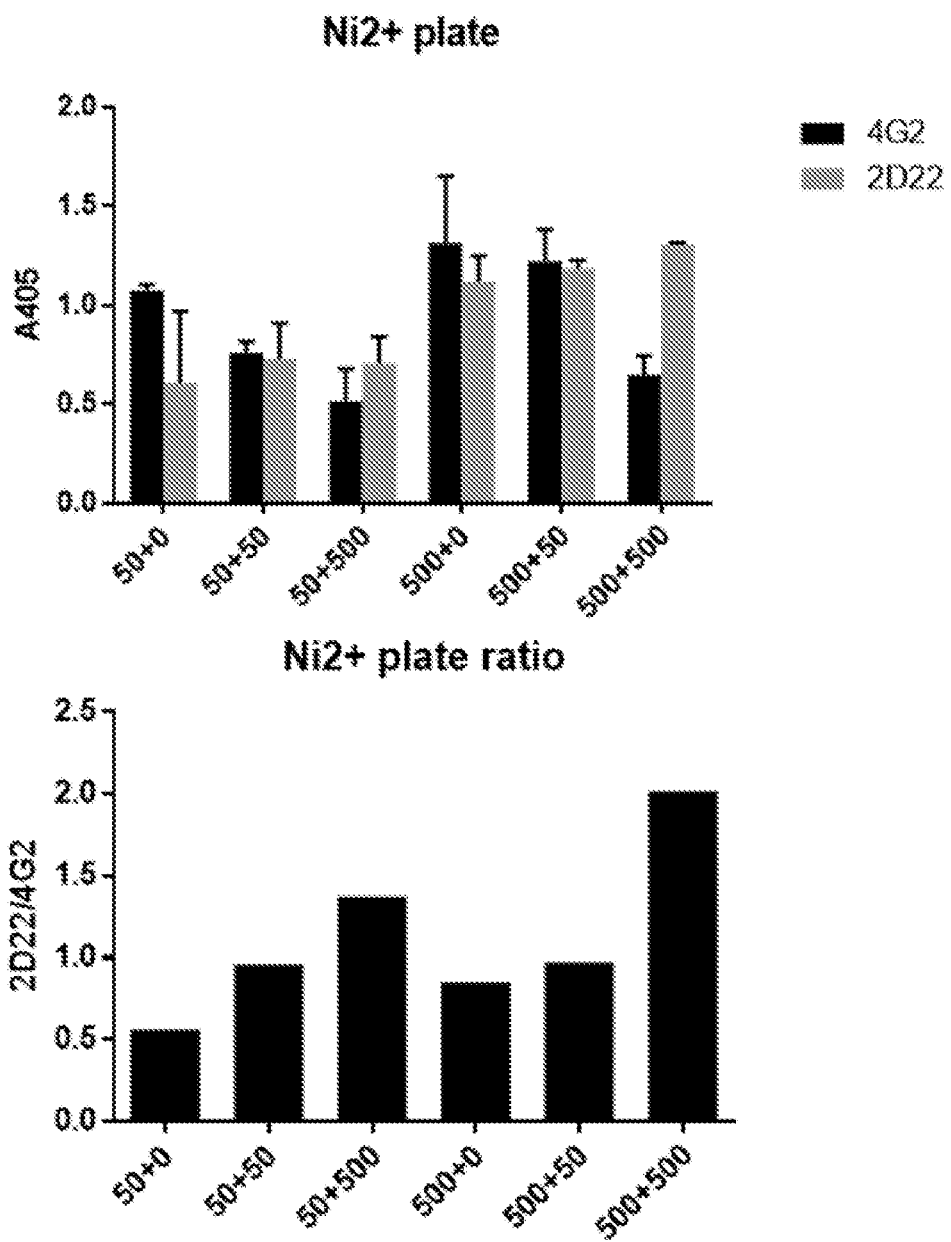

The dimerization of RecE on the ELISA plate requires the immobilization of the primary sRecE in a specific orientation. This was shown by duplicating the exact same experiment using ELISA plates that are not coated with $Ni^{2+}$ (FIG. 7). Primary sRecE was coated on ELISA plates in random conformations. The previously observed dimer formation between the primary and secondary RecE was not observed under any tested conditions, indicating that without the specific orientation of the primary RecE, dimerization cannot be enhanced.

We have discovered techniques to reconstruct complex quaternary neutralizing epitopes on artificial surfaces. When monomeric sRec is immobilized in a specific orientation, it is able to reconstruct dimer-dependent neutralizing 2D22 epitopes when it is exposed to high concentrations of a second monomeric sRecE. This will have great impact on the way that carrier-based vaccines such as nanoparticles carriers are designed and produced.

Figure 8:
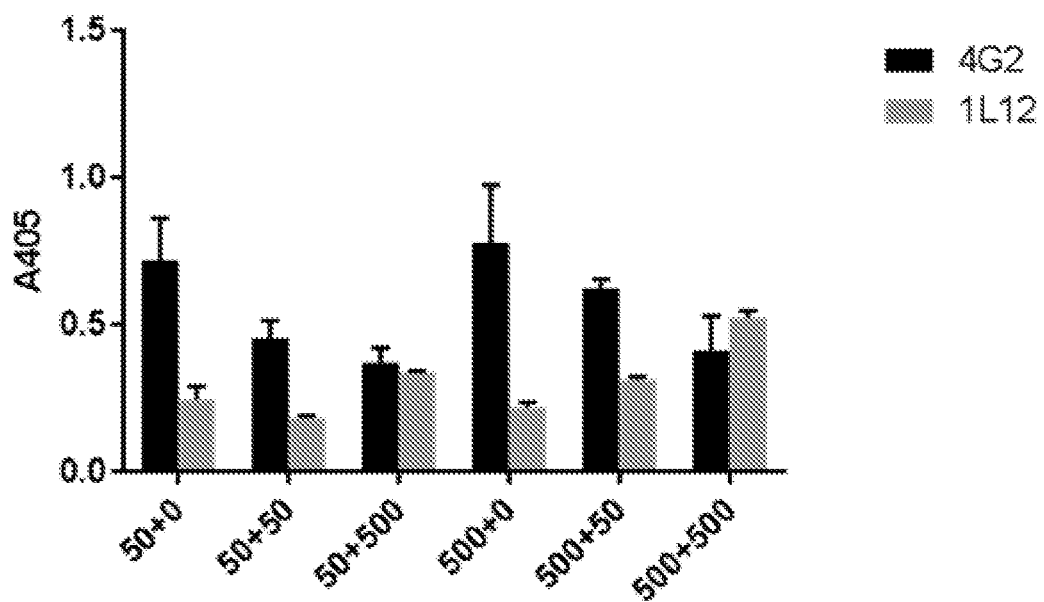
FIG. 8. IL12 can be used as a marker for RecE-dimer recreation. Low (50 ng/well) and high (500 ng/well) sRecE concentrations were loaded onto the $Ni^{2+}$-plates and reloaded with 0, 50, or 500 ng/well of sRecE.
Figure 8:
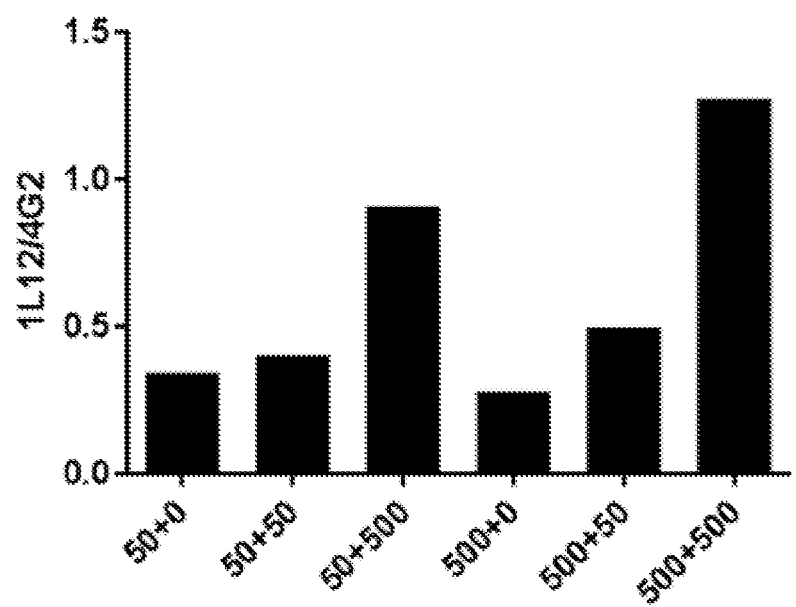

Studies were conducted to characterize the strongly neutralizing dengue virus antibody IL12. Results indicate that IL12 does not bind sRecE in regular ELISA and most likely recognizes quaternary epitopes located on both EDII and EDIII, which makes it similar to 2D22. We recreated protein dimer complexes on the $Ni^{2+}$-plates as described previously and subjected the RecE dimers to IL12 and 4G2, to see if we can use IL12 as a measure of RecE dimer recreation (FIG. 8).

The increasing dimerization pattern seen after the use of IL12 is identical to that of 2D22. This study supports the 2D22 data with another dengue virus monoclonal antibody. In addition, these results indicate that IL12 most likely recognized quaternary epitopes that are restored after protein dimerization.

The $Ni^{2+}$-His interaction used in the present studies to recreate the quaternary dimer-dependent 2D22 epitope serves well as proof the principle of primary sRecE immobilization and sRecE reload. Other interactions that can be used in the methods of this invention include, but are not limited to, biotin-avidin (streptavidin, NeutrAvidin) interactions, which have been exploited in many protein detection and purification studies. Biotin labels are stable and small and rarely interfere with the function or immunogenicity of labeled molecules. In the methods of this invention, we could use the avidin-biotin interactions to immobilize sRecE in a specific orientation and subsequently subject it to a protein reload.

Another option is a coiled-coil interaction. This biological method for creating heteroprotein dimers uses the coiled-coil interaction platform. It is based on the interaction of two α-helixes on the terminal ends of protein monomers. This technology can be used in the present invention to capture sRecE in a specific orientation on an artificial surface such as an ELISA plate or nanoparticle surface. First, the surface is coated with a α-helix stretch, which would bind an interacting α-helix on the C-terminal end of sRecE.

Temperature.

Figure 9:
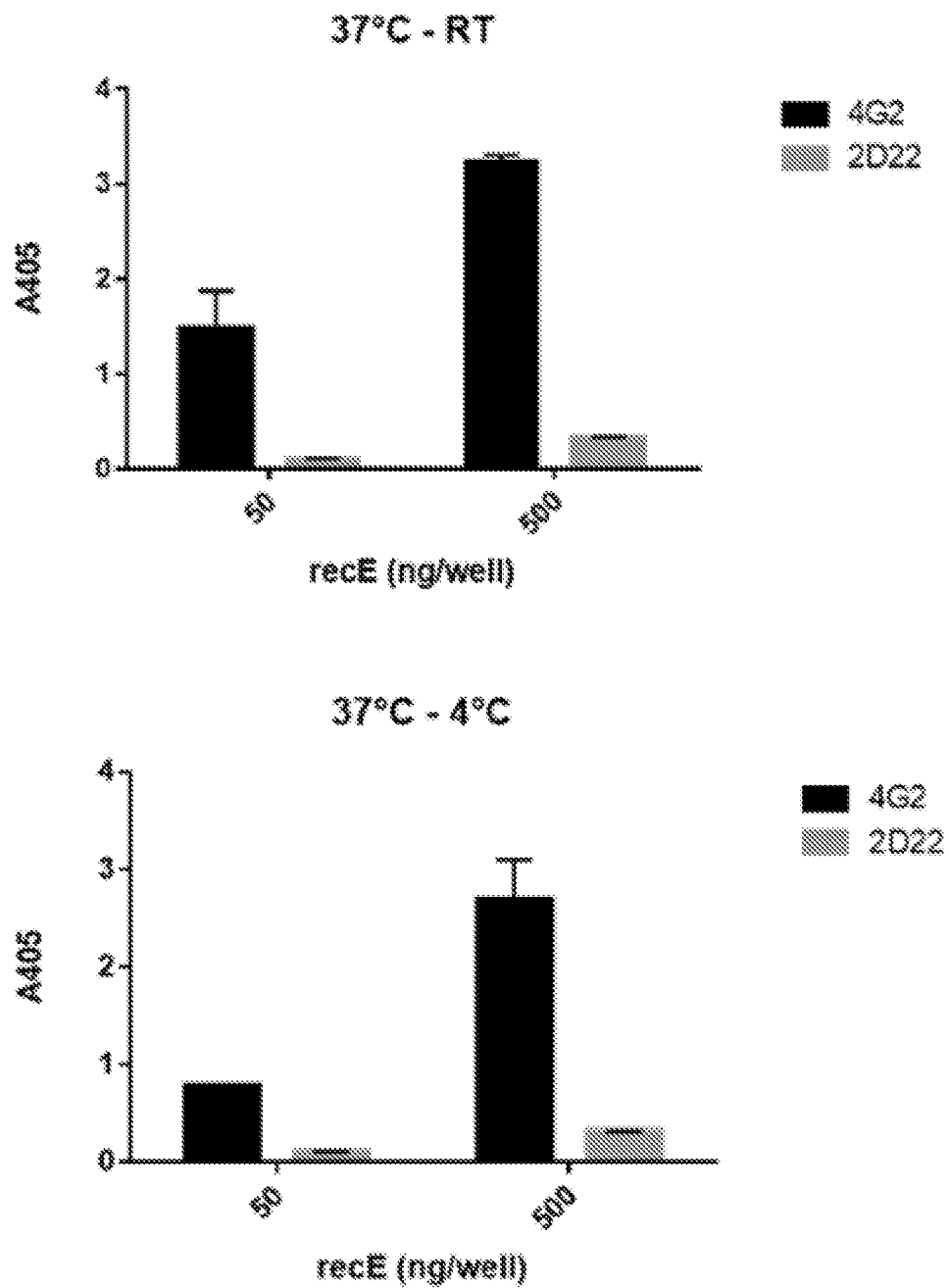
FIG. 9: Effect of temperature on 2D22 dimer signals. sRecE proteins were loaded at 37° C., RT or 4° C. and antibodies were incubated at 37° C., RT or 4° C., creating 6 different temperature regiments: 37° C.-RT, 37° C.-4° C., RT-37° C., RT-4° C., 4° C.-RT and 4° C.-37° C. The 2D22 signal is highest when sRecE is loaded at RT or 4° C. and is not influenced by the antibody incubation temperature.
Figure 9:
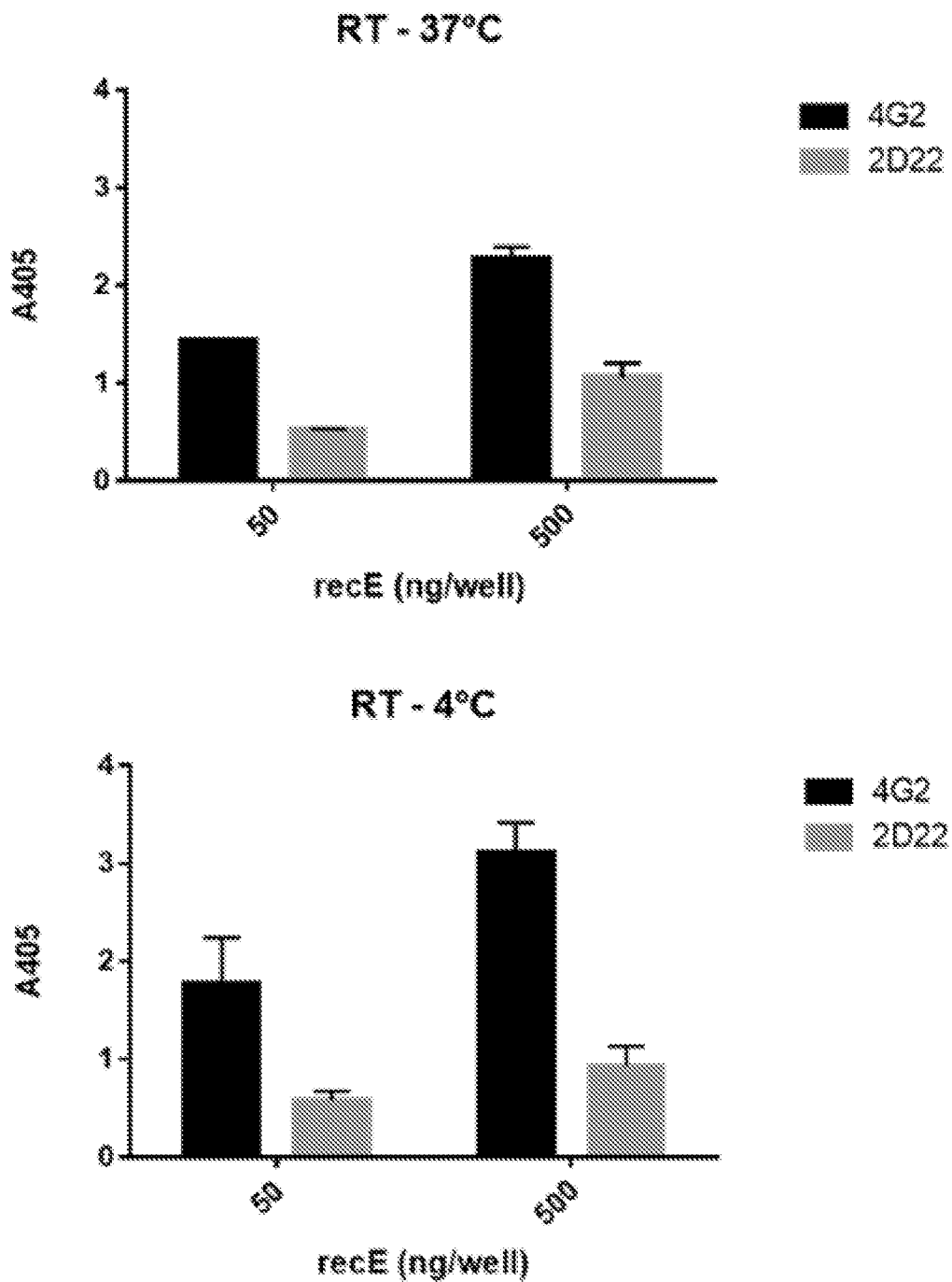
Figure 9:
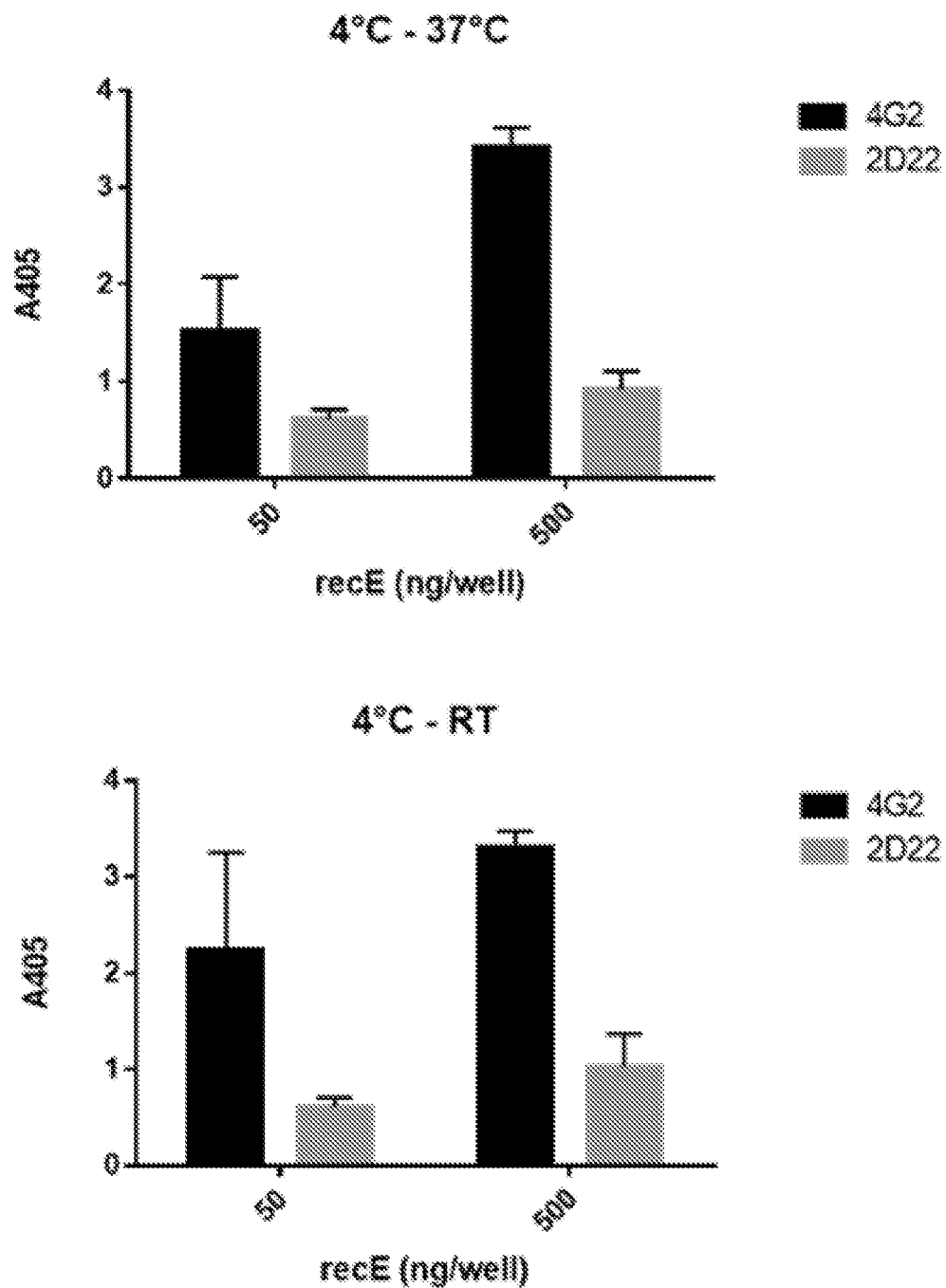

By performing the binding ELISA at different temperatures, we found that the temperature at which the proteins are loaded on the $Ni^{2+}$ plate affects the conformation of sRecE on the plate. We loaded 50 or 500 ng/well of sRecE on the plate at 37° C., room temperature (RT) or 4° C. and performed antibody-binding at the same varying temperatures (FIG. 9).

The 2D22 dimer signal was relatively low when sRecE was loaded at 37° C. and antibodies were incubated at RT or 4° C. (37° C.-RT and 37° C.-4° C.). However, when loaded at RT or at 4° C., the 2D22 signal clearly increased. This increased 2D22 signal was caused by the lower loading temperature and was not influenced by the antibody incubation temperature.

Figure 10:
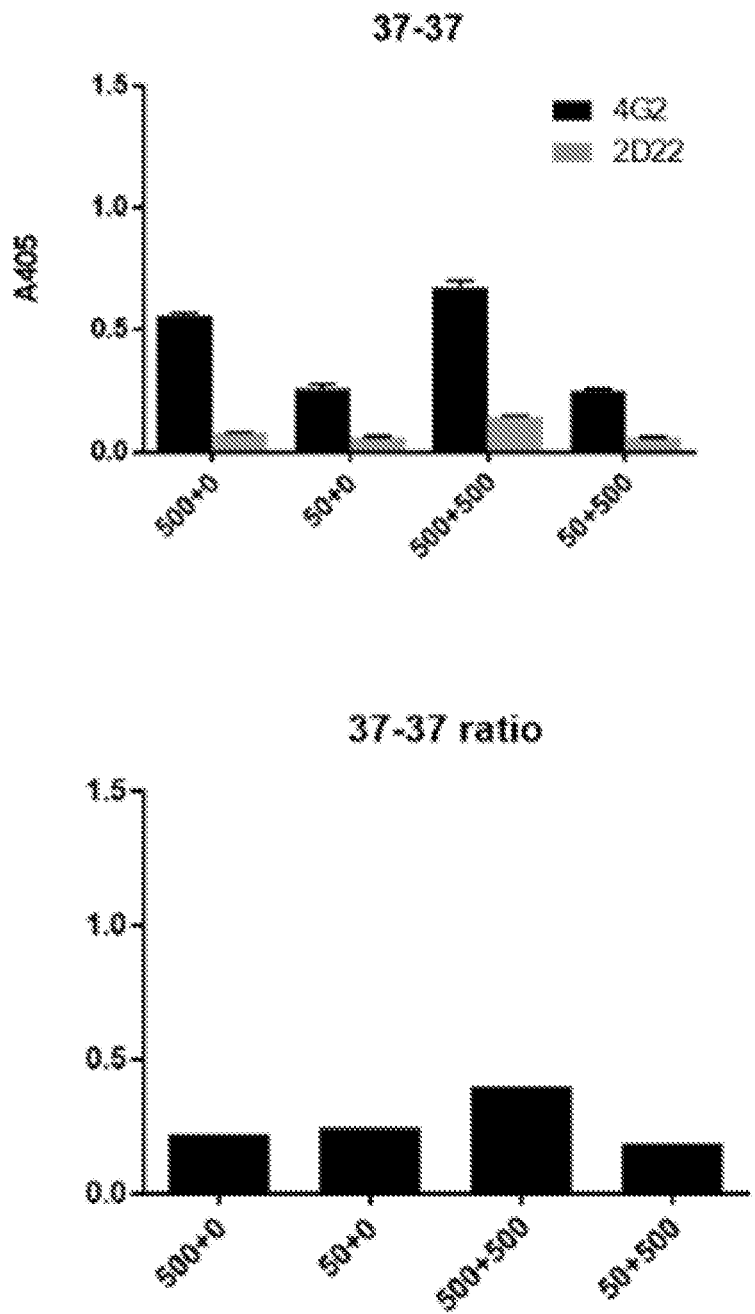
FIG. 10: Loading and reloading at RT improves rebuilding of dimers. sRecE proteins were loaded at 37° C. or at RT and were reloaded at 37° C. and RT, by the following temperature regimes: load at 37° C. and reload at 37° C. (37-37), load at 37° C. and reload at RT (37-RT), load at RT and reload at 37° C. (RT-37), load at RT and reload at RT (RT-RT). By loading and reloading at RT, the 2D22 signals increased and is higher than loading and reloading at 37° C. The ratios between the 4G2 and 2D22 (2D22/4G2) are depicted below the binding signal graphs.
Figure 10:
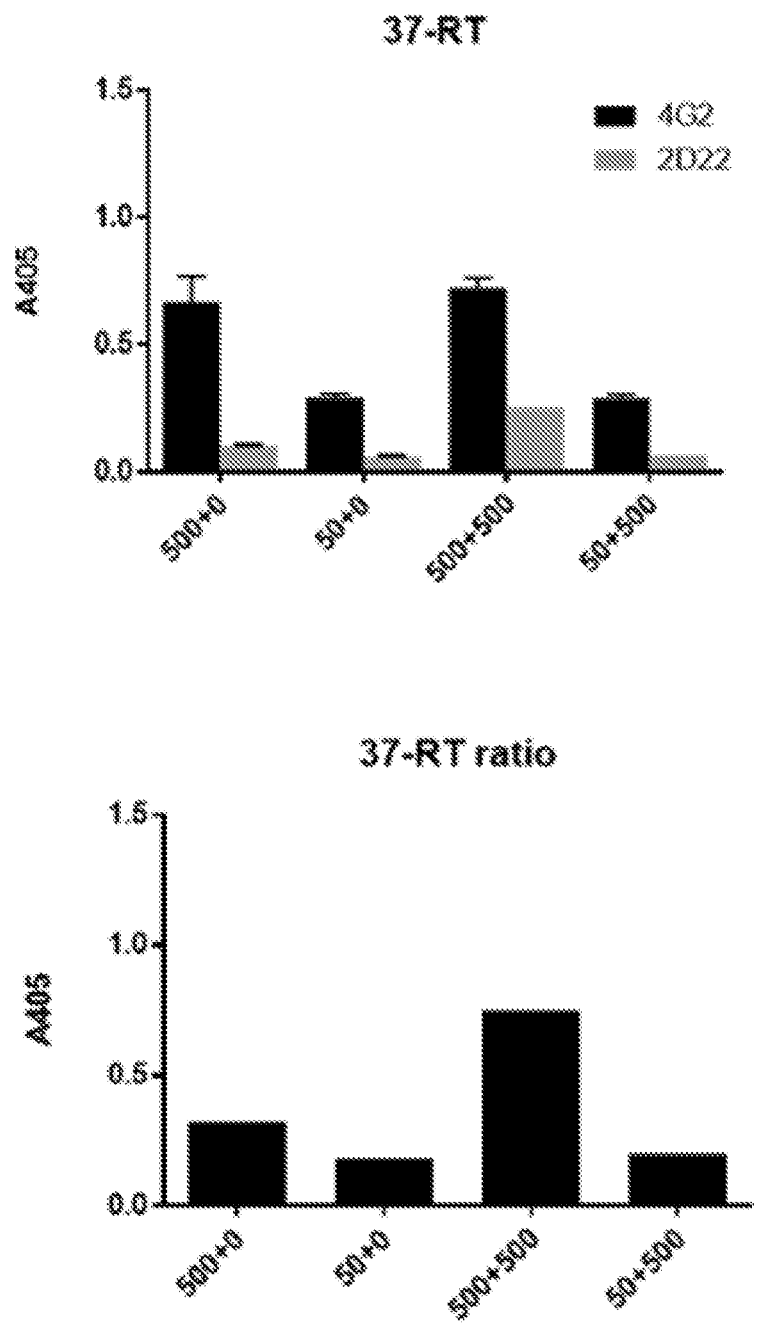
Figure 10:
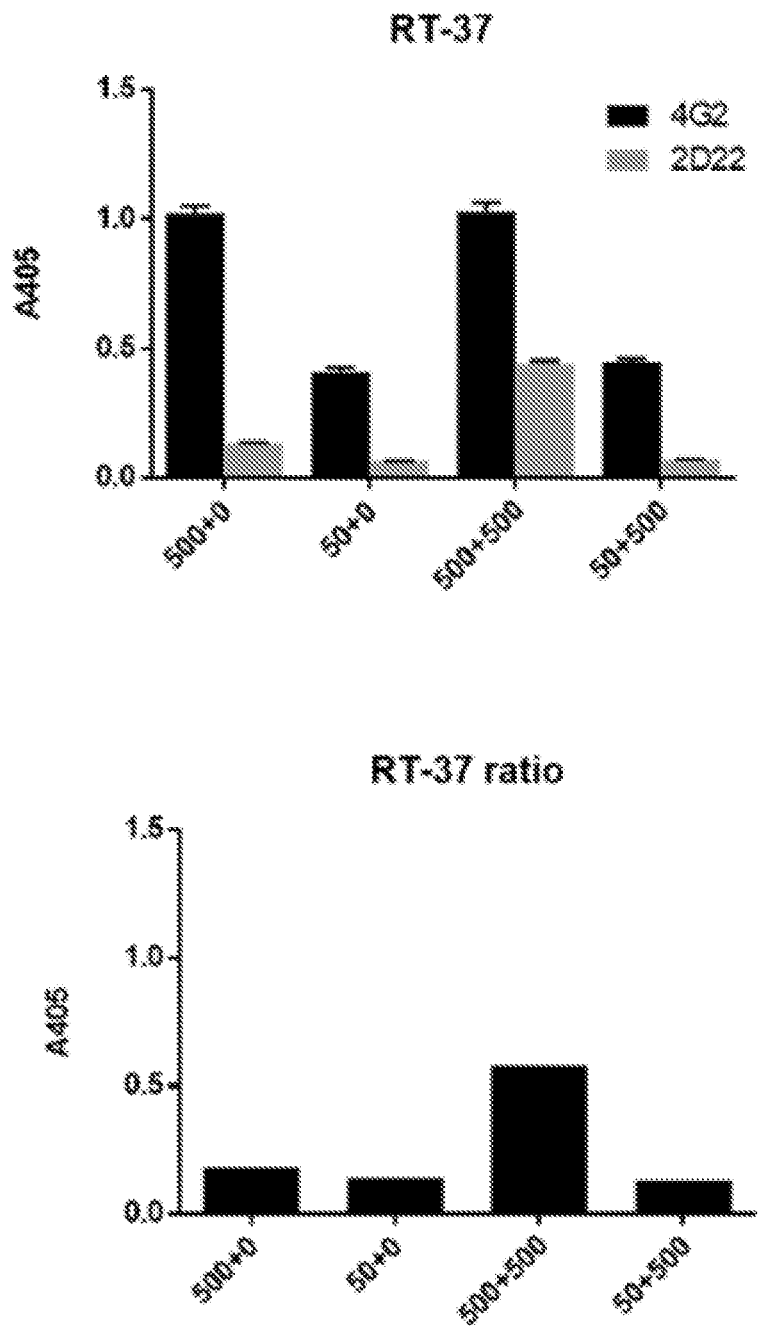
Figure 10:
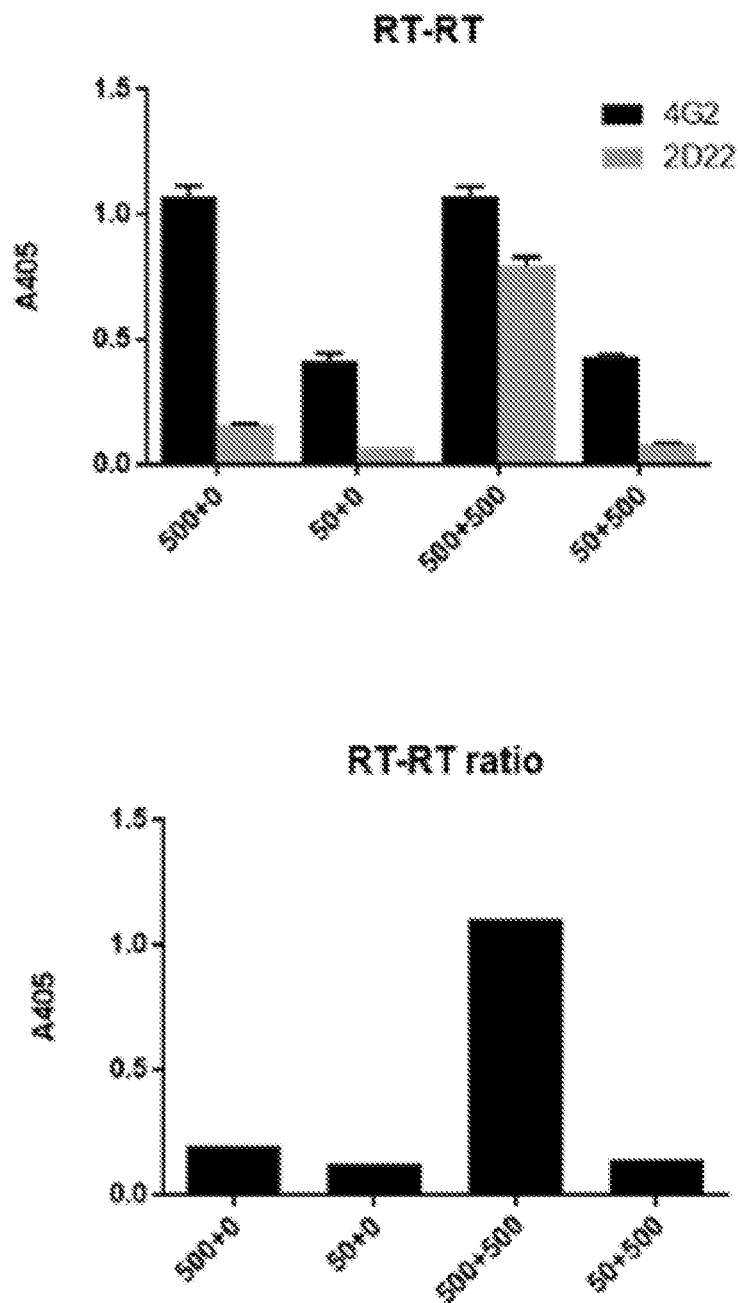

Next, we repeated the previously described dimer-building ELISA at 37° C. and RT to see if temperature also has an effect on rebuilding sRecE dimers. We varied the loading and reloading temperatures at 50 or 500 ng/well sRecE (FIG. 10) thus creating the following temperature regiments: Load at 37° C. and reload at 37° C. (37-37), load at 37° C. and reload at RT, load at RT and reload at 37° C., load at RT and reload at RT (RT-RT).

In all temperature regimens we see the increase of the 2D22 dimer signal when reloaded with 500 ng/well sRecE. In addition we see a strong effect of temperature on the 2D22 signal. All 2D22 levels, including the non-reloaded proteins, are higher at RT compared to 37° C. The loading temperature determines for a large part the formation of the dimers. However, we see that if the reloading step is performed at RT as well (37-RT and RT-RT), the 2D22 signals and dimers ratios are higher than when reloading is performed at 37° C. (37-37) and (RT-37).

In conclusion, the temperature during the rebuilding of DENV-E protein dimers from soluble monomers influences the efficiency by which the dimers are regenerated. This should be taken into account when the dimers are going to be rebuilt on nanoparticle surfaces for DENV-vaccine development purposes.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

Sequences

```
denv3 MRCVGVGNRDFVEGLSGATWVDVVLEHGGCVTTMAKNKPTLDIELQKTEATQLATLRKLC  60 denv1 MRCVGIGNRDFVEGLSGATWVDVVLEHGSCVTTMAKDKPTLDIELLKTEVTNPAVLRKLC  60 denv2 MRCIGISNRDFVEGVSGGSWVDIVLEHGSCVTTMAKNKPTLDFELIKTEAKQPATLRKYC  60 denv4 MRCVGVGNRDFVEGVSGGAWVDLVLEHGGCVTTMAQGKPTLDFELTKTTAKEVALLRTYC  60
      ***.*:.*****...*.*.**:.*: **  ..:  * **. * denv3 IEGKITNITTDSRCPTQGEAILPEEQDQNYVCKHTYVDRGWGNGCGLFGKGSLVTCAKFQ  120 denv1 IEAKISNTTTDSRCPTQGEATLVEEQDTNFVCRRTFVDRGWGNGCGLFGKGSLITCAKFK  120 denv2 IEAKLTNTTTESRCPTQGEPSLNEEQDKRFVCKHSMVDRGWGNGCGLFGKGGIVTCAMFT  120 denv4 IEASISNITTATRCPTQGEPYLKEEQDQQYICRRDVVDRGWGNGCGLFGKGGVVTCAKFL  120
      **..::*  :*****. * ****  .::*:: ***********.::* * denv3 CLESIEGKVVQHENLKYTVIITVHTGDQHQVGNET--QGVTAEITPQASTVEAILPEYGT  178 denv1 CVTKLEGKIVQYENLKYSVIVTVHTGDQHQVGNETTEHGTTATITPQAPTSEIQLTDYGA  180 denv2 CKKNMEGKVVQPENLEYTIVVTPHSGEEHAVGNDTGKHGKEIKVTPQSSITEAELTGYGT  180 denv4 CSGKITGNLVQIENLEYTVVVTVHNGDTHAVGNDTSNHGVTATITPRSPSVEVKLPDYGE  180
      * .: *:. *.*.::: * *.*: * ***.* :* :**::. * *. **

denv3 LGLECSPRTGLDFNEMILLTMKNKAWMVHRQWFFDLPLPWTSGATTETPTWNRKELLVTF  238 denv1 LTLDCSPRTGLDFNEMVLLTMEKKSWLVHKQWFLDLPLPWTSGASTSQETWNRQDLLVTF  240 denv2 VTMECSPRTGLDFNEMVLLQMENKAWLVHRQWFLDLPLPWLPGADTQGSNWIQKETLVTF  240 denv4 LTLDCEPRSGIDFNEMILMRMKKKTWLVHKQWFLDLPLPWTAGADTSEVHWNYKERMVTF  240
      : ::*.**:*:*****:*: *::*:*: :*.**** . *. *  :: :*** denv3 KNAHAKKQEVVVLGSQEGAMHTALTGATEIQNSGGTSIFAGHLKCRLKMDKLELKGMSYA  298 denv1 KTAHAKKQEVVVLGSQEGAMHTALTGATEIQTSGTTTIFAGHLKCRLKMDKLTLKGMSYV  300 denv2 KNPHAKKQDVVVLGSQEGAMHTALTGATEIQMSSGNLLFTGHLKCRLRMDKLQLKGMSYS  300 denv4 KVPHAKRQDVTVLGSQEGAMHSALAGATEVDSGDGNHMFAGHLKCKVRMEKLRIKGMSYT  300
      *  .***:*.*.********.*.****:.  ..  .:*:*****:::*: :*** denv3 MCLNTFVLKKEVSETQHGTILIKVEYKGEDAPCKIPFSTEDGQGKAHNGRLITANPVVTK  358 denv1 MCTGSFKLEKEVAETQHGTVLVQVKYEGTDAPCKIPFSSQDEKGVTQNGRLITANPIVTD  360 denv2 MCTGKFKVVKEIAETQHGTIVIRVQYEGDGSPCKIPFEIMDLEKRHVLGRLITVNPIVTE  360 denv4 MCSGKESIDKEMAETQHGTTVVKVKYEGAGAPCKVPIEIRDVNKEKVVGRIISSTPFAES  360
      **  ..* :  ::****  :::*:*:*  .:***.*:. *  *  **:*:  .*.. .
```

-continued

```
denv3 KEEPVNIEAEPPFGESNIVIGIGDKALKINWYKKGSS       395 denv1 KEKPVNIEAEPPFGESYIVVGAGEKALKLSWFKKGSS       397 denv2 KDSPVNIEAEPPFGDSYIIIGVDPGQLKLNWFKKGSS       397 denv4 TNSVTNIELEPPFGDSYIVIGVGDSALTLHWFRKGSS       397

Sources of each sequence
gi|1854036|gb|U88535.1|DVU88535 Dengue virus type 1 clone WestPac,
complete genome gi|280987261|gb|GU289914.1| Dengue virus 2 strain S16803, complete
genome gi|118406818|gb|DQ863638.1| Dengue virus 3 strain CH53489, complete
genome gi|6978317|gb|M14931.2|DENSTRA Dengue virus type 4 polyprotein
precursor, gene, complete cds DV2 16681 STRUCTURALS
1          CAPSID
MNNQRKKAKNTPFNMLKRERNRVSTVQQLTKRFSLGMLQGRGPLKLFMALVAFLRFL
TIPPTAGILKRWGTIKKSKAIN 100 C ANCHOR  1                    PR
VLRGFRKEIGRMLNILNRRRSAGMHMLIPTVMAFHLTTRNGEPHMIVSRQEKGKSLLF
KTEDGVNMCTLMAMDLGE 90        M
LCEDTITYKCPLLRQNEPEDIDCWCNSTSTWVTYGTCTTMGEHRREKRSVALVPHVGM
GLETRTETWMSSEGAWKH 166 1      EDI/II
VQRIETWILRHPGFTMMAAILAYTIGTTHFQRALIFILLTAVTPSMTMRCIGMSNRDFVE
GVSGGSWVDIVLEHGSCVT

TMAKNKPTLDFELIKTEAKQPATLRKYCIEAKLTNTTTESRCPTQGEPSLNEEQDKRFVC
KHSMVDRGWGNGCGLFGK

GGIVTCAMFRCKKNMEGKVVQPENLEYTIVITPHSGEEHAVGNDTGKHGKEIKITPQSSI
TEAELTGYGTVTMECSPRTG

LDFNEMVLLQMENKAWLVHRQWFLDLPLPWLPGADTQGSNWIQKETLVTFKNPHAK
KQDVVVLGSQEGAMHTAL

291 LINKER 301          EDIII
TGATEIQMSSGNLLFTGHLKCRLRMDKLQLKGMSYSMCTGKFKVVKEIAETQHGTIVIR
VQYEGDGSPCKIPFEIMDLE

395        E STEM
KRHVLGRLITVNPIVTEKDSPVNIEAEPPFGDSYIIIGVEPGQLKLNWFKKGSSIGQMFET
TMRGAKRMAILGDTAWDF
                                451         E TM REIGON
495
```

| Heavy-chain |   |   |   |
|---|---|---|---|
| Fab 1 |   |   |   |
| Residue | A | C' | B# |
| P53 |   | T70 |   |
| I54 |   | T70 |   |
| F55 |   | T70 |   |
|   |   | A71 |   |
|   |   | S72 |   |
|   |   | R99 |   |
|   |   | I113 |   |
|   |   | K247 |   |

| Heavy-chain |   |   |
|---|---|---|
| G56 | T69 |   |
|   | T70 |   |
|   | A71 |   |
|   | S72 |   |
|   | I113 |   |
| G57 | A71 |   |
|   | S72 |   |
|   | R73 |   |
|   | C74 |   |
| Q65 |   | P384 |
|   |   | G385 |

| Heavy-chain | | | |
|---|---|---|---|
| G66 | | | P384 |
| | | | G385 |
| | | | Q386 |
| R67 | | | P384 |
| V68 | | | P384 |
| T69 | | | P384 |
| T71 | | T69 | |
| A72 | | T69 | |
| D73 | | N67 | |
| | | T68 | |
| | | T69 | |
| K74 | | N67 | |
| | | T68 | |
| | | T69 | |
| S75 | | T66 | |
| | | N67 | |
| | | T68 | |
| T76 | | N67 | |
| S84 | | | G328 |
| R99 | G152 | | |
| P100 | | G104 | |
| Q101 | | G102 | |
| | | N103 | |
| | | G104 | |
| S102 | | W101 | |
| | | G102 | |
| | | N103 | |
| | | G104 | |
| S102 | | | C105 |
| | M1 | | |
| I103 | | W101 | |
| | | G102 | |
| | | N103 | |
| | | G104 | |
| | | C105 | |
| D105 | | G104 | |
| D109 | G152 | | |
| | N153 | | |

| Fab 2 | | | |
|---|---|---|---|
| Residue | B | B' | A |
| I52 | | G104 | |
| P53 | | T70 | |
| I54 | | K247 | |
| F55 | | T70 | |
| | | A71 | |
| | | S72 | |
| | | I113 | |
| | | K246 | |
| | | K247 | |
| | | Q248 | |
| G56 | | T69 | |
| | | T70 | |
| | | A71 | |
| | | S72 | |
| G57 | | T70 | |
| | | A71 | |
| | | S72 | |
| | | R73 | |
| | | C74 | |
| A58 | | A71 | |
| | | S72 | |
| | | R73 | |
| G66 | | | D225 |
| | | | Q227 |
| T71 | | T69 | |
| A72 | | T69 | |
| | | T70 | |
| D73 | | N67 | |
| | | T68 | |
| | | T69 | |
| | | T70 | |
| R74 | | N67 | |
| | | T68 | |
| | | T69 | |
| S75 | | N67 | |
| | | T68 | |
| | | T66 | |
| T76 | | N67 | |
| R99 | G152 | | |
| P100 | | G104 | |
| Q101 | | G102 | |
| | | N103 | |
| | | G104 | |
| S102 | | G102 | |
| | | N103 | |
| | | G104 | |
| | V151 | | |
| | G152 | | |
| I103 | | W101 | |
| | | G102 | |
| | | N103 | |
| | | G104 | |
| F104 | | G102 | |
| | | G104 | |

| Fab 3 | | | |
|---|---|---|---|
| Residue | C | A' | B |
| I52 | | N103 | |
| P53 | | T70 | |
| I54 | | T70 | |
| | | K247 | |
| F55 | | T70 | |
| | | A71 | |
| | | S72 | |
| | | I113 | |
| | | K246 | |
| | | K247 | |
| G56 | | T69 | |
| | | T70 | |
| | | A71 | |
| | | S72 | |
| G57 | | A71 | |
| | | S72 | |
| | | R73 | |
| | | C74 | |
| A58 | | A71 | |
| | | S72 | |
| | | R73 | |
| G66 | | | T226 |
| T71 | | T69 | |
| | | A71 | |
| A72 | | T69 | |
| | | T70 | |
| D73 | | N67 | |
| | | T68 | |
| | | T69 | |
| | | T70 | |
| R74 | | N67 | |
| | | T68 | |
| S75 | | T69 | |
| | | T66 | |
| | | N67 | |
| | | T68 | |
| | | T69 | |
| T76 | | N67 | |
| P100 | G152 | | |
| Q101 | G152 | | |
| S102 | V151 | | |
| | G152 | | |
| | | G102 | |
| I103 | R2 | | |
| | V151 | | |
| | G152 | | |
| | | W101 | |
| | | G102 | |
| | | N103 | |
| | | G104 | |
| F104 | | W101 | |
| | | G102 | |

Heavy-chain (continued)

| | |
|---|---|
| | N103 |
| | G104 |
| D105 | G104 |

B#: mol B from adjacent raft

Light-chain

Fab 1

| Residue | A | C' | A# |
|---|---|---|---|
| S2 | | | |
| S26 | | | G177 |
| | | | S298 |
| | | | Y299 |
| S27 | | | K295 |
| | | | S298 |
| G30 | | | S298 |
| | Q325 | | |
| S31 | | | S298 |
| | K307 | | |
| | V309 | | |
| | Q325 | | |
| N32 | V309 | | |
| Y33 | S363 | | |
| R51 | E148 | | |
| | N149 | | |
| | S363 | | |
| N52 | D362 | | |
| | S363 | | |
| R54 | N149 | | |
| P56 | N153 | | |
| | D154 | | |
| | T155 | | |
| S57 | N153 | | |
| | D154 | | |
| | T155 | | |
| K67 | D362 | | |
| S68 | D362 | | |
| G69 | E327 | | |
| D94 | K310 | | |
| S95 | | G177 | |
| | | Y178 | |
| | | G179 | |
| | | K291 | |
| | | L292 | |
| | | Q293 | |
| L96 | | Y178 | |
| | | G179 | |
| | | T180 | |
| | | K291 | |
| S97 | | K291 | |

Fab 2

| Residue | B | B' | A |
|---|---|---|---|
| G30 | Q325 | | |
| S31 | V309 | | |
| | Q325 | | |
| | P364 | | |
| N32 | S363 | | |
| | P364 | | |
| Y33 | S363 | | |
| | P364 | | |
| R51 | S363 | | |
| N52 | D362 | | |
| | S363 | | |
| P56 | G152 | | |
| | N153 | | |
| S57 | N153 | | |
| | D154 | | |
| K67 | D362 | | |
| G69 | E327 | | |

Fab 3

| Residue | C | A' | B |
|---|---|---|---|
| S31 | V309 | | |
| | Q325 | | |
| N32 | V309 | | |
| N52 | S363 | | |
| P56 | T155 | | |
| S57 | T155 | | |
| K67 | D362 | | |
| S68 | D362 | | |
| G69 | E327 | | |
| | D362 | | |

A#: mol A from adjacent raft

Interacting residues between the Fab 5J7 and the E proteins on a raft.

| HMAb 5J7 | E protein mols | | | HMAb 5J7 | E protein mols | | |
|---|---|---|---|---|---|---|---|
| H-chain | A | B | B' | L-chain | A | B | B' |
| T35 | Q52 | K308 | | S35 | E123 | | |
| | Q131 | E309 | | | | | |
| | E133 | | | | | | |
| | N134 | | | | | | |
| S37 | | K308 | G106 | S37 | E123 | | |
| | | | | | K200 | | |
| S38 | Q52 | | | R38 | E123 | | |
| | Q131 | | | | K200 | | |
| | N134 | | | | N201 | | |
| I59 | A54 | | | Q99 | K58 | | |
| | | | | | T223 | | |
| V61 | A54 | | C74 | Y100 | K58 | | |
| | | | | | P227 | | |
| F62 | A54 | | R73 | I101 | T223 | | |
| | | | C74 | | T224 | | |
| K81 | | | | W101 | | | |
| S82 | | Q148 | | | | | |
| | | K307 | | | | | |
| S84 | | K307 | | | | | |
| R105 | Q52 | | | | | | |
| K107 | L53 | | | | | | |
| | T55 | | | | | | |
| L109 | T51 | | | | | | |
| | T274 | | | | | | |
| L110 | A50 | | | | | | |
| | L53 | | | | | | |
| | K128 | | | | | | |
| | V130 | | | | | | |
| | L196 | | | | | | |
| | T274 | | | | | | |
| | I276 | | | | | | |
| F111 | T198 | | | | | | |
| | T274 | | | | | | |
| R113 | E126 | | | | | | |

Interaction interface between Fab 1F4 and DENV1 E protein.

| DENV-1 E-protein | | Fab 1F4 | |
|---|---|---|---|
| Segment | Amino acid residue | L-chain | H-chain |
| 46-52 | L46 | L77 | |
| | K47 | Y74, D75, D76, L77 | |
| | E49 | D75, K90 | |

Interaction interface between Fab 1F4 and DENV1 E protein.

| Segment | DENV-1 E-protein Amino acid residue | Fab 1F4 L-chain | Fab 1F4 H-chain |
|---|---|---|---|
| | T51 | G53 | |
| | N52 | S49, G53 | |
| 136-138 | K136 | N54, N55 | Y112 |
| | S138 | Y74 | |
| 155-165 | S155 | L78, P79, S80 | |
| | T156 | S80 | |
| | E157 | | Y36, R102, K104, D117 |
| | T160 | | K104, Y111 |
| | T161 | Y74 | K104, Y114 |
| | A162 | | Y111 |
| | T163 | Y74 | Y111, Y112 |
| | T165 | | Y112 |
| 170-177 | T170 | | K109 |
| | T171 | | P110, Y111 |
| | E172 | | T108, Y111 |
| | I173 | | Y111 |
| | Q174 | | Y57, N105 |
| | T176 | | T32, Y36, K104 |
| | D177 | | T32 |
| 272-276 | S273 | S89, S91 | |
| | G274 | S89 | |
| | T275 | D75, D76 | |
| | T276 | K90, S91 | |

What is claimed is:

1. A method of producing recombinant soluble dengue virus E ectodomain dimers, comprising:
   a) preparing a first recombinant soluble monomeric dengue virus E ectodomain comprising a functional first linking moiety at one terminus;
   b) contacting the first ectodomain with a second linking moiety that associates with the first linking moiety, wherein the second linking moiety is attached to a solid substrate, thereby attaching the ectodomain to the solid substrate in a specific orientation;
   c) contacting the first ectodomain attached to the solid substrate with a second recombinant monomeric dengue virus E ectodomain lacking a functional first linking moiety under conditions whereby dimerization of the first ectodomain and second ectodomain can occur;
   d) detaching the recombinant soluble dengue virus E ectodomain dimers from the solid substrate; and
   e) collecting the recombinant soluble dengue virus E ectodomain dimers.

2. The method of claim 1, wherein the first linking moiety and second linking moiety are selected from the group consisting of: 1) a histidine tag (HIS) and $Ni^{2+}$, respectively; 2) biotin and avidin, respectively; and 3) a primary α-helix and a secondary α-helix, respectively.

3. The method of claim 1, wherein the dengue virus is selected from the group consisting of dengue virus serotype 1 (DENV-1), dengue virus serotype 2 (DENV-2), dengue virus serotype 3 (DENV-3), and dengue virus serotype 4 (DENV-4).

4. A method of producing a recombinant dengue virus E ectodomain dimer attached to a carrier, comprising:
   a) preparing a first recombinant monomeric dengue virus E ectodomain comprising a functional first linking moiety at one terminus;
   b) contacting the first ectodomain with a second linking moiety that associates with the first linking moiety, wherein the second linking moiety is attached to a carrier, thereby attaching the ectodomain to a solid substrate in a specific orientation; and
   c) contacting the first ectodomain attached to the carrier with a second recombinant monomeric dengue virus E ectodomain lacking a functional first linking moiety under conditions whereby dimerization of the first ectodomain and second ectodomain can occur.

5. The method of claim 4, wherein the first linking moiety and second linking moiety are selected from the group consisting of: 1) a histidine tag (HIS) and $Ni^{2+}$, respectively; 2) biotin and avidin, respectively; and 3) a primary α-helix and a secondary α-helix, respectively.

6. The method of claim 4, wherein the dengue virus is selected from the group consisting of dengue virus serotype 1 (DENV-1), dengue virus serotype 2 (DENV-2), dengue virus serotype 3 (DENV-3), and dengue virus serotype 4 (DENV-4).

* * * * *

UNITED STATES PATENT AND TRADEMARK OFFICE
CERTIFICATE OF CORRECTION

PATENT NO. : 10,772,948 B2  
APPLICATION NO. : 15/766304  
DATED : September 15, 2020  
INVENTOR(S) : Metz et al.

Page 1 of 1

It is certified that error appears in the above-identified patent and that said Letters Patent is hereby corrected as shown below:

In the Specification

Column 1, Lines 7-10: delete the entirety of the STATEMENT OF PRIORITY and replace with the following:
This application is a 35 U.S.C. § 371 national phase application of International Application Serial No. PCT/US2016/052706, filed September 20, 2016, which claims the benefit, under 35 U.S.C. § 119(e), of U.S. Provisional Application No. 62/238,496, filed October 7, 2015, the entire contents of each of which are incorporated by reference herein.

Column 1, Lines 14-20: delete the entirety of the STATEMENT OF GOVERNMENT SUPPORT and replace with the following:
This invention was made with government support under Grant No. U19 AI109784-01 awarded by the National Institutes of Health. The United States Government has certain rights in the invention.

Column 20, Line 25: delete "10°" and insert -- $10^0$ --

Column 27, Line 13, Left Column of the Heavy-Chain Table: delete "K74" and insert -- R74 --

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*